(12) United States Patent
Murase

(10) Patent No.: US 9,879,097 B2
(45) Date of Patent: Jan. 30, 2018

(54) METHOD FOR PRODUCING ACTIVATED SUGAR CHAIN DERIVATIVE AND ACTIVATED SUGAR CHAIN DERIVATIVE PRODUCED THEREFROM

(71) Applicant: GLYTECH, INC., Kyoto (JP)

(72) Inventor: Takefumi Murase, Kyoto (JP)

(73) Assignee: Glytech, Inc., Kyoto (JP)

( * ) Notice: Subject to any disclaimer, the term of this patent is extended or adjusted under 35 U.S.C. 154(b) by 35 days.

(21) Appl. No.: 14/784,923

(22) PCT Filed: Apr. 17, 2014

(86) PCT No.: PCT/JP2014/060946
§ 371 (c)(1),
(2) Date: Oct. 15, 2015

(87) PCT Pub. No.: WO2014/171514
PCT Pub. Date: Oct. 23, 2014

(65) Prior Publication Data
US 2016/0075799 A1 Mar. 17, 2016

(30) Foreign Application Priority Data
Apr. 19, 2013 (JP) .................................. 2013-088902

(51) Int. Cl.
| | | |
|---|---|---|
| C12P 19/26 | (2006.01) | |
| C08B 37/00 | (2006.01) | |
| C12P 19/04 | (2006.01) | |
| C12N 9/82 | (2006.01) | |
| C07H 15/12 | (2006.01) | |

(52) U.S. Cl.
CPC ............ *C08B 37/006* (2013.01); *C07H 15/12* (2013.01); *C08B 37/00* (2013.01); *C12N 9/82* (2013.01); *C12P 19/04* (2013.01); *C12P 19/26* (2013.01)

(58) Field of Classification Search
None
See application file for complete search history.

(56) References Cited

U.S. PATENT DOCUMENTS

2007/0060543 A1* 3/2007 Kajihara ................ C07H 13/00
514/54

FOREIGN PATENT DOCUMENTS

| | | |
|---|---|---|
| EP | 0413675 A2 | 2/1991 |
| EP | 1650226 | 4/2006 |
| EP | 2926829 | 10/2015 |
| EP | 2980098 | 2/2016 |
| JP | 10120697 A | 5/1998 |
| JP | 2004533404 A | 11/2004 |
| WO | 198804323 | 6/1988 |
| WO | 2005010053 A1 | 2/2005 |
| WO | 2007034183 A2 | 3/2007 |
| WO | 2010122162 A1 | 10/2010 |

OTHER PUBLICATIONS

Paul et al., "Synthesis of novel glycolipids derived from glycopyranosyl azides and N-(beta-glycopyranosyl)azidoacetamides" Tetrahedron Letters (2008) vol. 49 pp. 6356-6359.*
Yamamoto et al., "Chemical Synthesis of a Glycoprotein Having an Intact Human Complex-Type Sialyloligosaccharide under the Boc and Fmoc Synthetic Strategies" Journal of the American Chemical Society (2008) vol. 130 pp. 501-510.*
Krenkova J. et al, Multidimensional system enabling deglycosylation of proteins using a capillary reactor with peptide-N-glycosidase F immobilized on a porous polymer monolith and hydrophilic interaction liquid chromatography-mass spectrometry of glycans, J Chromatogr A. Apr. 10, 2009;1216 (15): 3252-3259.
Rasmussen et al, Identification nd derivatization of (Oligosaccry) amines obtained by treatment asparagine-linked glycopeptides with N-glycanase enzyme,Journal Am Chem Soc, 1992, v114,No. 3, pp. 1124-1126.
Tarentino AL et al, Enzymatic deglycosylation of asparagine-linked glycans: purification, properties, and specificity of oligosaccharide-cleaving enzymes from Flavobacterium meningosepticum, Methods Enzymol, 1994; v230: pp. 44-57.
Englebretsen, D. R. et al, "A Novel Thioether Linker: Chemical Synthesis of a HIV1 Protease Analogue by Thioether Ligation", Tetrahedron Lett., 1995, vol. 36, No. 48, pp. 8871-8874.
Manger et al, "1-N-Glycyl .beta.-oligosaccharide Derivatives as Stable Intermediates for the Formation of Glycoconjugate Probes", Biochemistry, 1992, vol. 31, pp. 10724-10732.
Sekiya et al, "Derivatization for Stabilizing Sialic Acids in MALDI-MS.", Anal. Chem. 2005, vol. 77, No. 15, pp. 4962-4968.
Wong et al, "Analysis of Carbohydrate-Protein Interactions with Synthetic N-linked Neoglycoconjugate Probes.", Biochem J. Dec. 15, 1993; 296(Pt 3): 817-825.

(Continued)

*Primary Examiner* — Eric Olson
(74) *Attorney, Agent, or Firm* — Dennis A. Bennett; John Desper

(57) ABSTRACT

When manufacturing a sugar chain compound having an activating group, there was a problem with the ammonium carbonate method that is the conventional technology that during the process of introducing an amino group at the reducing terminal of the sugar chain, the unit sugar located at the reducing terminal of the sugar chain is subjected to ring-opening, thus causing a mixture of α and β anomers to be produced. The present invention provides a method for manufacturing a sugar chain compound having an activating group with high β selectivity using a compound having a sugar chain asparagine structure as the source material by cleaving the sugar chain from the sugar chain peptide so that the reducing terminal of the sugar chain and the nitrogen atom derived from the asparagine side chain will remain in a bound state, and introducing an activating group to said nitrogen atom while retaining not only the covalent bond between the reducing terminal of said sugar chain and said nitrogen atom but also the β configuration. A novel sugar chain compound which is a β anomer and has an activating group is also provided as a compound of the present invention.

12 Claims, 3 Drawing Sheets

(56) References Cited

OTHER PUBLICATIONS

Murase, Takefumi, Method for producing activated sugar-chain derivative, and activated sugar-chain derivative, EP2987863-EESR, issued Mar. 21, 2017.

Murase T. et al., Efficient and systematic synthesis of a small glycoconjugate library having human complex type oligosaccharides, Carbohydr Res. Apr. 21, 2009;344(6):762-70. XP026067891.

* cited by examiner

[Figure 1]
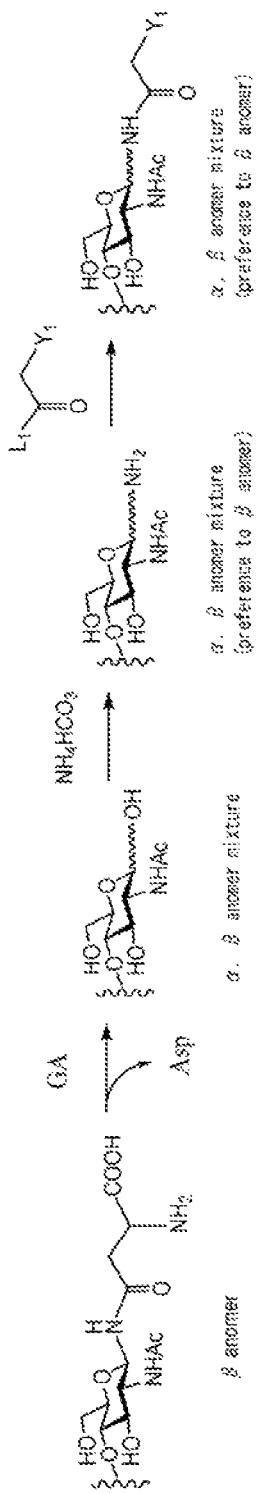

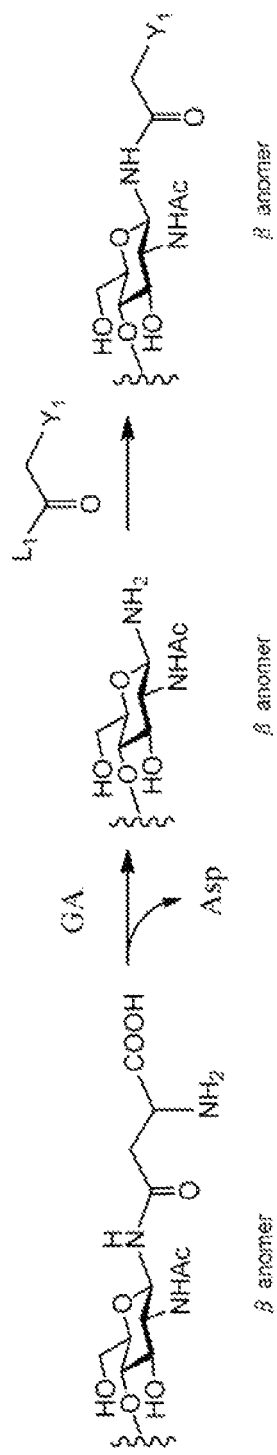
[Figure 2]

[Figure 3]
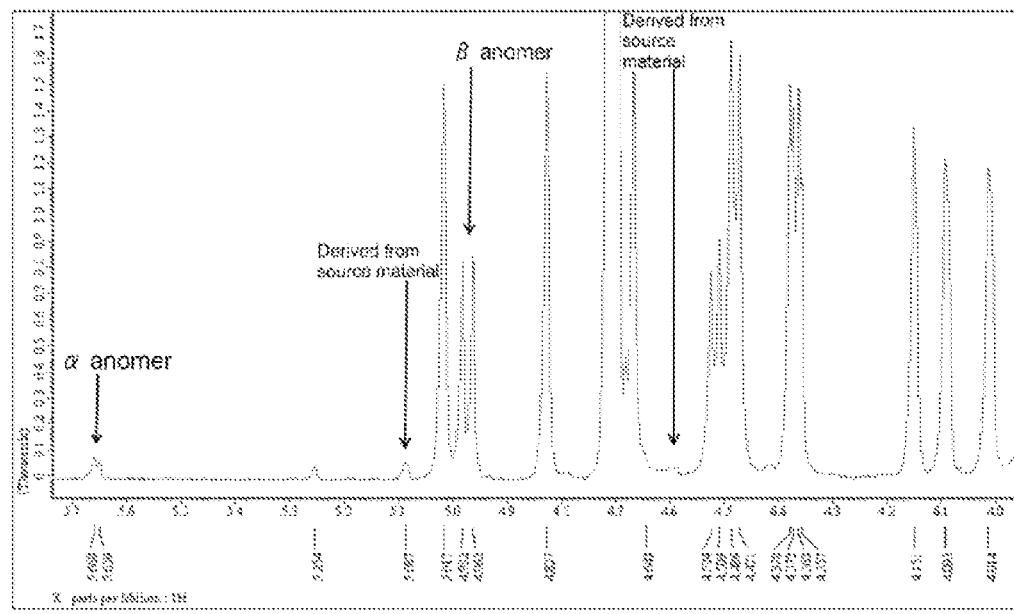
[Figure 4]
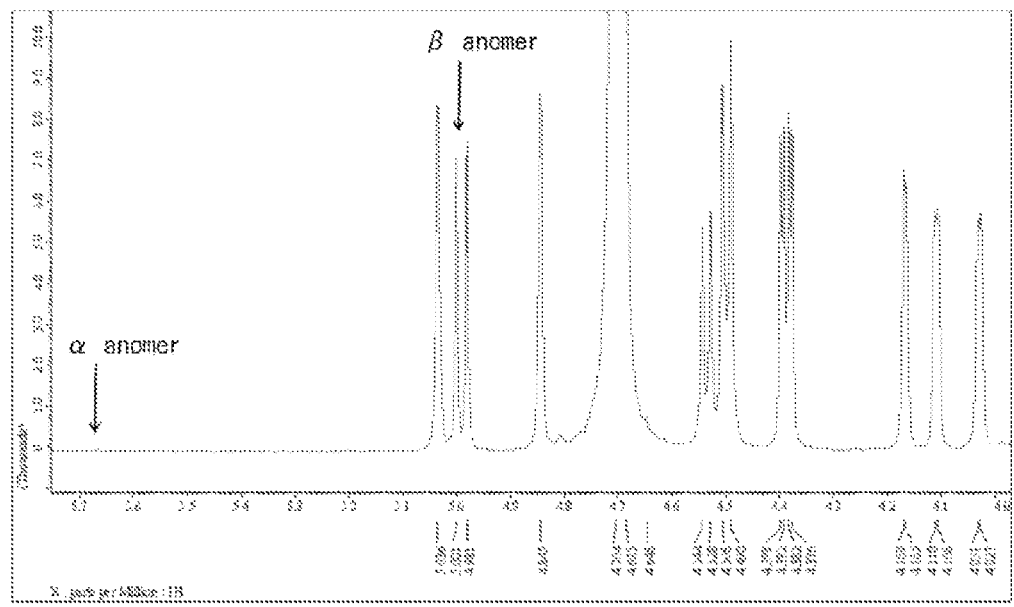

SEQUENCE LISTING

<160> NUMBER OF SEQ ID NOS: 1

<210> SEQ ID NO 1
<211> LENGTH: 6
<212> TYPE: PRT
<213> ORGANISM: Artificial
<220> FEATURE:
<223> OTHER INFORMATION: SGP
<220> FEATURE:
<221> NAME/KEY: CARBOHYD
<222> LOCATION: (4)..(4)
<223> OTHER INFORMATION: sugar chain added

<400> SEQUENCE: 1

Lys Val Ala Asn Lys Thr
1               5

METHOD FOR PRODUCING ACTIVATED SUGAR CHAIN DERIVATIVE AND ACTIVATED SUGAR CHAIN DERIVATIVE PRODUCED THEREFROM

This application is a U.S. National Stage Application under 35 U.S.C. §371 of International Application No. PCT/JP2014/060946, filed Apr. 17, 2014, which claims priority to Japan Application No. 2013-088902 filed Apr. 19, 2013. Each of the above-referenced applications is expressly incorporated by reference herein its entirety.

TECHNICAL FIELD

The present invention relates to a method for producing an activated sugar chain derivative compound and an activated sugar chain derivative compound produced therefrom.

BACKGROUND ART

A sugar chain is generally those where a monosaccharide and a monosaccharide are linearly bound via a bond called a glycosyl bond. It is known that various sugar chains have important roles in vivo. Sugar chains often exist in vivo as glycoconjugates bound to a peptide, a protein, a lipid, and the like.

In particular, glycopeptides or glycoproteins that exist in vivo are known to have a sugar chain having a particular structure bound thereto at a particular amino add of the peptide. These sugar chains are known to cause various influences on activity or in vivo kinetics etc. of the peptide (protein), depending on differences in their structure.

These sugar chains or glycosylated peptides are also being used as pharmaceuticals, but it is known that the sugar chain structure will be ununiform when a glycosylated peptide is prepared by a cell line. Since variability in drug effect may be caused when the sugar chain structure is ununiform, there is high necessity for adding separated and purified or chemically synthesized sugar chains with uniform structure to peptides. However, in order to bind separated and purified or chemically synthesized sugar chains to other substances such as peptides, a functional group necessary for binding must be added to the sugar chain as necessary.

As a method for adding a functional group necessary for binding with other substances (also referred to herein as an activating group) to the sugar chain, for example, a method of separating and purifying a sugar chain having an —OH group at the reducing terminal of the sugar chain from a natural egg yolk etc., introducing an amino group at the reducing terminal of the sugar chain by the ammonium carbonate method, and adding an activating group to the said amino group has been performed (see e.g. Patent Literatures 1 and 2 and Non-Patent Literatures 1 and 2). However, with such a method, there was a problem that during the process of introducing an amino group to the sugar chain, the amino group is introduced via ring-opening and ring-dosing of the unit sugar located at the reducing terminal of the sugar chain, and therefore a mixture of α and β anomers is produced even though the configuration of the binding between the sugar chain and the peptide in a naturally-occurring glycopeptide is β-form.

CITATION LIST

[Patent Literature 1] International Publication No. 2005/010053
[Patent Literature 1] EP 0413675 A2
[Non-Patent Literature 1] Biochemistry (1992), Vol. 31, pp. 10724-10732
[Non-Patent Literature 2] Biochemical J. (1993), Vol. 296, pp. 817-825

SUMMARY OF THE INVENTION

Problems to be Solved by the Invention

When manufacturing a sugar chain compound having an activating group, there was a problem with the ammonium carbonate method that is the conventional technology that during the process of introducing an amino group at the reducing terminal of the sugar chain, the unit sugar located at the reducing terminal of the sugar chain is subjected to ring-opening, thus causing a mixture of α and β anomers to be produced.

Means for Solving the Problems

In order to solve the above problem, the present inventors performed extensive investigations for a method for β-selectively manufacturing a sugar chain compound having an activating group at the reducing terminal of the sugar chain. As a result, the present inventors found a method for manufacturing a sugar chain compound having an activating group as a β anomer using a compound having a sugar chain asparagine structure as the source material by cleaving the sugar chain from the sugar chain peptide so that the reducing terminal of the sugar chain and the nitrogen atom derived from the asparagine side chain will remain in a bound state, and introducing an activating group to said nitrogen atom while retaining not only the covalent bond between the reducing terminal of said sugar chain and said nitrogen atom but also the β configuration. As a result of extensive investigation regarding the above manufacturing method, the present inventors also found a novel sugar chain compound which is a β anomer having an activating group as a compound of the present invention.

In other words, the present invention relates to a method for manufacturing a compound represented by the following Formula (1a):

G-NH—CO—CH$_2$—Y$^1$     (1a)

(wherein G represents a sugar chain, Y$^1$ represents an activating group, and G and NH are bound so that the nitrogen atom of NH is bound to the reducing terminal of said sugar chain in β configuration).

The manufacturing method of the present invention may be a method for manufacturing a compound represented by the above Formula (1a) that comprises the following steps (a)-(b).

In the manufacturing method of the present invention, step (a) may be a step represented as below:

(a) a step of applying a sugar chain asparagine hydrolase under basic conditions on a compound having the sugar chain asparagine structure represented by the following Formula (2):

G-Asn     (2)

(wherein G represents a sugar chain, Asn represents an asparagine, and G and Asn are bound so that the nitrogen atom of the side chain of said asparagine is bound to the reducing terminal of said sugar chain in β configuration) to obtain a compound represented by the following Formula (3):

G-NH$_2$     (3)

(wherein G represents a sugar chain, NH$_2$ represents an amino group, and G and NH$_2$ are bound so that the nitrogen atom derived from the nitrogen atom of the side chain of said asparagine is bound to the reducing terminal of said sugar chain in β configuration).

In the manufacturing method of the present invention, step (b) may be a step represented as below:

(b) a step of reacting the compound represented by said Formula (3) obtained in step (a) with a compound represented by the following Formula (4):

$$L^1\text{-CO—CH}_2\text{—Y}^1 \qquad (4)$$

(wherein $L^1$ is a leaving group, and $Y^1$ is an activating group.)

Moreover, one embodiment of the method of the present invention for manufacturing a sugar chain compound having an activating group relates to a method for manufacturing a compound represented by the following Formula (1b):

$$\text{G-NH—CO—CH}_2\text{—Y}^2 \qquad (1b)$$

(wherein G represents a sugar chain, $Y^2$ represents an activating group, and G and NH are bound so that the nitrogen atom of NH is bound to the reducing terminal of said sugar chain in β configuration).

In the manufacturing method of the present invention, a method for manufacturing a compound represented by the above Formula (1b) may comprise the following steps (a)-(c).

In the method of the present invention for manufacturing the compound represented by Formula (1b), step (a) may be a step represented as below:

(a) a step of applying a sugar chain asparagine hydrolase under basic conditions on a compound having the sugar chain asparagine structure represented by the following Formula (2):

$$\text{G-Asn} \qquad (2)$$

(wherein G represents a sugar chain, Asn represents an asparagine, and G and Asn are bound so that the nitrogen atom of the side chain of said asparagine is bound to the reducing terminal of said sugar chain in β configuration) to obtain a compound represented by the following Formula (3):

$$\text{G-NH}_2 \qquad (3)$$

(wherein G represents a sugar chain, $NH_2$ represents an amino group, and G and $NH_2$ are bound so that the nitrogen atom derived from the nitrogen atom of the side chain of said asparagine is bound to the reducing terminal of said sugar chain in β configuration).

In the method of the present invention for manufacturing the compound represented by Formula (1b), step (b) may be a step represented as below:

(b) a step of reacting the compound represented by said Formula (3) obtained in step (a) with a compound represented by the following Formula (5):

$$L^1\text{-CO—CH}_2\text{—Z} \qquad (5)$$

(wherein $L^1$ is a leaving group, and Z is a halogen atom.)

In the method of the present invention for manufacturing the compound represented by Formula (1b), step (c) may be a step represented as below:

(c) a step of reacting the compound obtained in step (b) with a compound represented by the following Formula (6a) or Formula (6b):

$$L^2\text{-Y}^2 \qquad (6a)$$

(wherein $L^2$ is a leaving group, and $Y^2$ is an activating group)

$$L^3Y^3 \qquad (6b)$$

(wherein $L^3$ is a cation, $Y^3$ is an anion of said activating group $Y^2$, and $L^3Y^3$ is a salt of $L^3$ and $Y^3$).

In one embodiment of the method of the present invention for manufacturing a compound represented by the above Formula (1a), $Y^1$ may be those selected from the group consisting of a bromine atom, a chlorine atom, an iodine atom, SH, $N_3$, $NHNH_2$, $SHCH_2CH_2NH_2$, and $CH(OMe)_2$.

In one embodiment of the method of the present invention for manufacturing a compound represented by the above Formula (1a), $Y^1$ may be those selected from the group consisting of a bromine atom, a chlorine atom, an iodine atom, and $CH(OMe)_2$.

In one embodiment of the method of the present invention for manufacturing a compound represented by the above Formula (1b), Z may be a bromine atom, and $Y^2$ may be those selected from the group consisting of a chlorine atom, an iodine atom, SH, $N_3$, $NHNH_2$, and $SHCH_2CH_2NH_2$.

In one embodiment of the method of the present invention for manufacturing a sugar chain compound having an activating group, said sugar chain asparagine hydrolase in said step (a) may be glycosylasparaginase (GA) and/or peptide: N-glycanase (PNGase).

In one embodiment of the method of the present invention for manufacturing a sugar chain compound having an activating group, said sugar chain asparagine hydrolase in said step (a) may be those immobilized to a carrier.

In one embodiment of the method of the present invention for manufacturing a sugar chain compound having an activating group, said sugar chain asparagine hydrolase in said step (a) is immobilized to a carrier, and further, the method may comprise the following step (d) after said step (a) and before said step (b):

(d) a step of separating said sugar chain asparagine hydrolase immobilized to a carrier from the reaction system.

In one embodiment of the method of the present invention for manufacturing a sugar chain compound having an activating group, said step (a) may be performed under a temperature condition of 0° C. to 40° C.

In one embodiment of the method of the present invention for manufacturing a sugar chain compound having an activating group, said step (a) may be performed under a temperature condition of 0° C. to 10° C.

In one embodiment of the method of the present invention for manufacturing a sugar chain compound having an activating group, said sugar chain may be an N-linked sugar chain.

In one embodiment of the method of the present invention for manufacturing a sugar chain compound having an activating group, said sugar chain may be an N-linked complex-type sugar chain.

In one embodiment of the method of the present invention for manufacturing a sugar chain compound having an activating group, said sugar chain may be a sugar chain selected from the group consisting of a disialo sugar chain, an asialo sugar chain, and a DiGlcNAc sugar chain.

In one embodiment of the method of the present invention for manufacturing a sugar chain compound having an activating group, said sugar chain may be those represented by the following Formula (7):

[Chemical Formula 1]

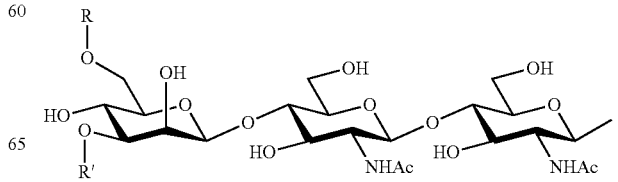

(7)

(wherein R and R' are each independently selected from the group consisting of sugar chains represented by the following Formula (8a) to Formula (8f):

[Chemical Formula 2]

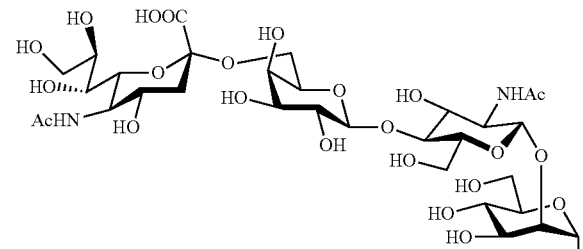

(8a)

[Chemical Formula 3]

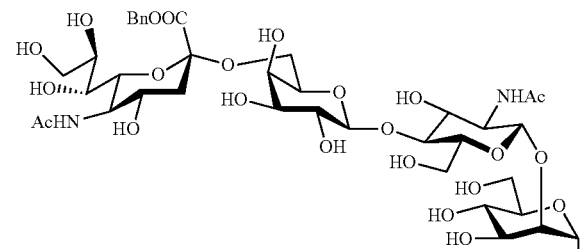

(8b)

[Chemical Formula 4]

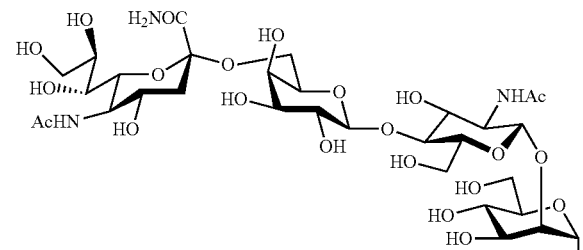

(8c)

[Chemical Formula 5]

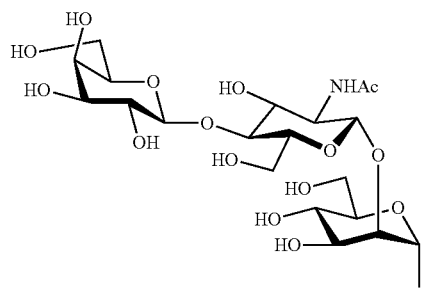

(8d)

[Chemical Formula 6]

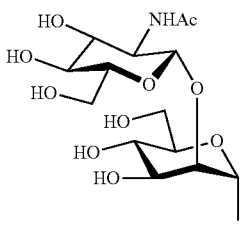

(8e)

[Chemical Formula 7]

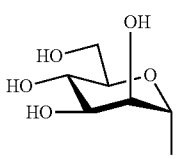

(8f)

In one embodiment of the method of the present invention for manufacturing a sugar chain compound having an activating group, said sugar chain may be a disialo sugar chain wherein the side chain carboxylic add of the sialic add configuring said disialo sugar chain is protected by esterification or amidation.

In another embodiment of the present invention, the present invention relates to a compound represented by the following Formula (1c) as a sugar chain compound having an activating group:

[Chemical Formula 8]

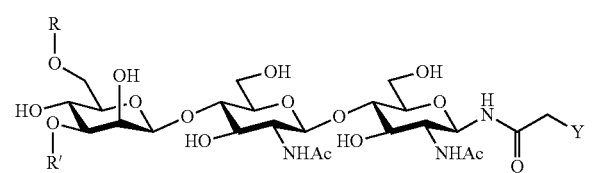

(1c)

(wherein Y is selected from the group consisting of a bromine atom, a chlorine atom, an iodine atom, SH, $N_3$, $NHNH_2$, $SHCH_2CH_2NH_2$, and $CH(OMe)_2$, and R and R' are each independently selected from the group consisting of sugar chains represented by the following Formula (8a) to Formula (8f):

[Chemical Formula 9]

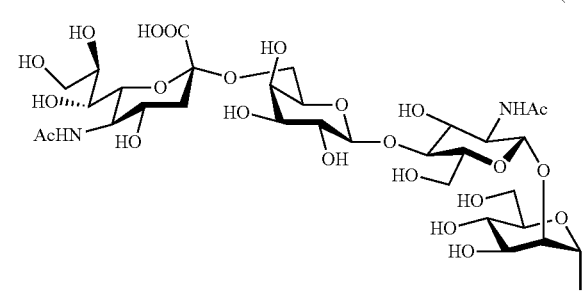

(8a)

-continued

[Chemical Formula 10]

(8b)

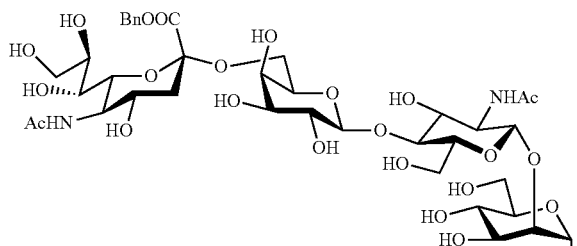

[Chemical Formula 11]

(8c)

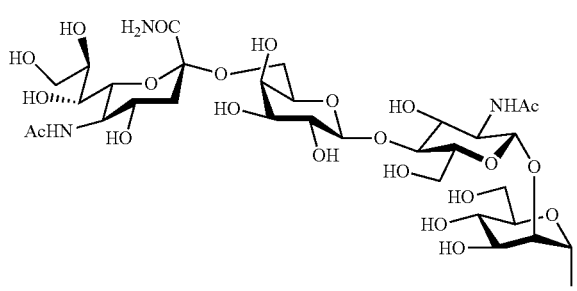

[Chemical Formula 12]

(8d)

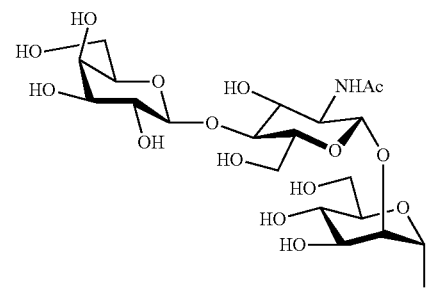

[Chemical Formula 13]

(8e)

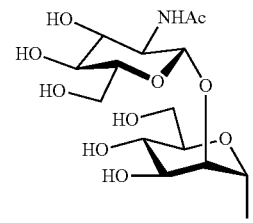

[Chemical Formula 14]

(8f)

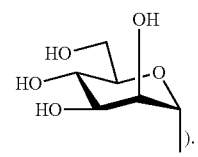

One embodiment of the sugar chain compound having an activating group of the present invention may be a compound represented by said Formula (1c), wherein Y is selected from the group consisting of a chlorine atom, an iodine atom, SH, $N_3$, $NHNH_2$, $SHCH_2CH_2NH_2$, and $CH(OMe)_2$, and R and R' are each independently selected from sugar chains represented by said Formula (8a) to Formula (8f).

One embodiment of the sugar chain compound having an activating group of the present invention may be a compound represented by said Formula (1c), wherein Y is selected from the group consisting of an iodine atom, SH, $N_3$, $NHNH_2$, $SHCH_2CH_2NH_2$, and $CH(OMe)_2$, and R and R' are each independently selected from sugar chains represented by said Formula (8a) to Formula (8f).

One embodiment of the sugar chain compound having an activating group of the present invention may be a compound represented by said Formula (1c), wherein Y is selected from the group consisting of SH, $N_3$, $NHNH_2$, $SHCH_2CH_2NH_2$, and $CH(OMe)_2$, and R and R' are each independently selected from sugar chains represented by said Formula (8a) to Formula (8f).

One embodiment of the sugar chain compound having an activating group of the present invention may be a compound represented by said Formula (1c), wherein Y is selected from the group consisting of an iodine atom, SH, $N_3$, $NHNH_2$, $SHCH_2CH_2NH_2$, and $CH(OMe)_2$, and R and R' are identical and selected from sugar chains represented by said Formula (8a) to Formula (8e).

One embodiment of the sugar chain compound having an activating group of the present invention may be a compound represented by said Formula (1c), wherein Y is selected from the group consisting of a chlorine atom, an iodine atom, SH, $N_3$, $NHNH_2$, $SHCH_2CH_2NH_2$, and $CH(OMe)_2$, and R and R' are both a sugar chain represented by said Formula (8b).

One embodiment of the sugar chain compound having an activating group of the present invention may be a compound represented by said Formula (1c), wherein Y is selected from the group consisting of a chlorine atom, an iodine atom, SH, $N_3$, $NHNH_2$, $SHCH_2CH_2NH_2$, and $CH(OMe)_2$, and R and R' are both a sugar chain represented by said Formula (8c).

In one embodiment of the method of the present invention for manufacturing a sugar chain compound having an activating group, the basic condition, the reaction temperature, the reaction time, the compounds to be reacted, and the like for performing each step may be any combination of those indicated above.

In one embodiment of the sugar chain compound having an activating group of the present invention, Y, R and R' in the formula may be any combination of those selected from those indicated above.

Effects of the Invention

The present invention, as a method for manufacturing a sugar chain derivative having an activating group, has an effect of enabling the introduction of an activating group while retaining β configuration at the reducing terminal of the sugar chain, i.e. an effect of having superior β selectivity compared to the ammonium carbonate method that is the conventional technology.

By virtue of an embodiment, the present invention, as a method for manufacturing a sugar chain derivative having an activating group, has an effect of enabling manufacture of a sugar chain derivative with higher β anomer purity in a shorter time compared to the conventional ammonium carbonate method.

The present invention, as a method for manufacturing a sugar chain derivative having an activating group, also has an effect of enabling manufacture of a sugar chain derivative with high β anomer purity at a higher yield by employing low temperature conditions.

The present invention also has an effect of enabling manufacture of a sugar chain derivative with high β anomer purity more easily and at a higher yield by immobilizing an enzyme to a solid phase.

Further, by employing the sugar chain derivative of the present invention having an activating group and reading it with a functional group that is present in the side chain of a peptide etc. or that is introduced in the side chain of a peptide etc., a glycopeptide and/or a glycoprotein having uniform structure sugar chains which are β anomers on the peptide can be manufactured.

BRIEF DESCRIPTION OF THE DRAWINGS

FIG. 1 is a reaction formula showing the synthetic scheme of the conventional technology.

FIG. 2 is a reaction formula showing the synthetic scheme of the present invention.

FIG. 3 is the $^1$H-NMR spectrum of asialo sugar chain-NH—AcBr synthesized with the method of conventional technology.

FIG. 4 is the $^1$H-NMR spectrum of asialo sugar chain-NH—AcBr synthesized with the method of the present invention.

DESCRIPTION OF EMBODIMENTS

The embodiments of the present invention will now be described in detail below.

The present invention relates to a method for manufacturing a sugar chain compound having an activating group.

A sugar chain compound having an activating group herein is those having an amino group at the reducing terminal of the sugar chain and having an activating group further bound to said amino group. The binding of an activating group to a sugar chain compound may also be referred to herein as introducing an activating group to a sugar chain compound. An activating group refers to a substituent having a functional group with high reactivity that can be used for binding a sugar chain to other substances such as a peptide, a protein, and a lipid. The sugar chain compound having an activating group herein, in the sense that it is derivatized in order to bind a sugar chain to other substances, can also be referred to as an activated sugar chain derivative, or simply a sugar chain derivative.

The method for manufacturing a sugar chain compound having an activating group herein comprises steps (a) and (b).

Step (a) is a step of applying a sugar chain asparagine hydrolase on a sugar chain asparagine or a sugar chain peptide comprising a sugar chain asparagine to obtain a sugar chain amine compound wherein the amino group derived from the asparagine side chain is bound to the reducing terminal of the sugar chain.

Step (b) is a step of reacting the sugar chain amine compound obtained in step (a) with a compound having an activating group to introduce the activating group to the nitrogen atom of the amino group present at the reducing terminal of the sugar chain.

Step (a) is characterized in employing a sugar chain asparagine hydrolase under basic conditions.

The conventional technology also sometimes employed an enzyme when separating and purifying a sugar chain from a glycopeptide to cleave and separate the sugar chain from the sugar chain asparagine (see e.g. the above Patent Literature 1), but with such a conventional method, a sugar chain having not an amino group but a hydroxyl group at the reducing terminal of the sugar chain was obtained by the sugar chain asparagine hydrolase. In addition, it was known that a sugar chain having a hydroxyl group at its reducing terminal yielded a mixture of a sugar chain having an —OH group in a configuration (i.e. an α anomer) and a sugar chain having an —OH in β configuration (i.e. a β anomer).

In addition, a method of substituting the hydroxyl group at the reducing terminal with an amino group by the ammonium carbonate method had been performed on a sugar chain as a mixture of α and β anomers of such sugar chains having an —OH group at the reducing terminal. It was known that the reaction was performed at a certain degree of high temperature for a certain degree of extended time with the ammonium carbonate method in order to allow action with ammonium carbonate. The sugar chain compound obtained as a result was also not sufficiently high in β anomer purity.

As a result of extensive investigations by the present inventors for a method for manufacturing a sugar chain compound having an activating group with high β selectivity, it was surprisingly found that by employing basic conditions when employing a sugar chain asparagine hydrolase, the amino group derived from the side chain nitrogen atom of asparagine can be retained at the reducing terminal of the sugar chain, and superior β selectivity can be realized.

In other words, the present inventors found, as one aspect of the present invention, that significant β selectivity can be further realized by employing basic conditions when employing a sugar chain asparagine hydrolase, as well as performing the reaction at a low temperature.

The present inventors also found, as one aspect of the present invention, that significant β selectivity can be further realized by employing basic conditions when employing a sugar chain asparagine hydrolase, as well as performing the reaction in a short period of time.

The present inventors also found, as one aspect of the present invention, that significant β selectivity can be further realized by employing basic conditions when employing a sugar chain asparagine hydrolase, as well as performing the reaction at a low temperature and in a short period of time.

As a result of extensive investigations by the present inventors, as described in the Examples below, realization of extremely high β-selective reaction to an extent that β selectivity is higher than 94%, more preferably to an extent that is higher than 99% was enabled by the manufacturing method of the present invention.

Moreover, according to the manufacturing method of the present invention, since a step of aminating the sugar chain after separating and purifying the sugar chain will become unnecessary, the cost and time that was necessary for amination in the conventional method could be reduced.

Further, according to the manufacturing method of the present invention, it is possible to greatly reduce the time for obtaining a sugar chain amine compound from a sugar chain asparagine or a sugar chain peptide.

In addition, in the conventional ammonium carbonate method, the degradation reaction of the sugar chain or the deprotection reaction of the protecting group of the sugar chain had occurred and reduced the yield during reaction at a high temperature of 30° C.-50° C. for an extended time, whereas according to the manufacturing method of the present invention, such degradation or deprotection of the sugar chain could be prevented to allow for a manufacturing method with a higher yield.

In the manufacturing method of the present invention, a sugar chain compound having an activating group as the compound of interest can be shown as the compound represented by Formula (1a), the compound represented by Formula (1b), the compound represented by Formula (1c), and the like.

For example, the compound represented by Formula (1a) is as follows:

$$\text{G-NH—CO—CH}_2\text{—Y}^1 \tag{1a}$$

(wherein G represents a sugar chain, $Y^1$ represents an activating group, and G and NH are bound so that the nitrogen atom of NH is bound to the reducing terminal of said sugar chain in β configuration.)

These compounds can be referred to as those wherein an activating group (Y, $Y^1$, or $Y^2$) is bound to the reducing terminal of the sugar chain via —NH—CO—CH$_2$—.

As the source material compound employed for the manufacturing method of the present invention, "a compound having the sugar chain asparagine structure represented by Formula (2)" and the like can be shown.

$$\text{G-Asn} \tag{2}$$

(wherein G represents a sugar chain, Asn represents an asparagine, and G and Asn are bound so that the nitrogen atom of the side chain of said asparagine is bound to the reducing terminal of said sugar chain in β configuration.)

Here, "the sugar chain asparagine structure represented by Formula (2)" refers to those wherein the nitrogen atom of the side chain of asparagine is bound to the reducing terminal of the sugar chain in β configuration, and these are sometimes referred to herein as the "sugar chain asparagine structure." A "compound having the sugar chain asparagine structure represented by Formula (2)" includes a sugar chain asparagine composed of a sugar chain and asparagine, as well as a sugar chain asparagine-containing peptide having yet other amino adds bound by peptide bond on either ends of the sugar chain asparagine.

In other words, "a compound having the sugar chain asparagine structure represented by Formula (2)" can also be represented by the following Formula (2a):

$$(\text{Aa})n\text{-Asn(G)-(Aa)}m \tag{2a}$$

(wherein Aa represents any amino add, (Aa)n indicates that any n independently selected amino adds are bound by peptide bonds, (Aa)m indicates that any m independently selected amino adds are bound by peptide bonds, n and m are each independently an integer from 0 to 100, and Asn(G), similarly to Formula (2), indicates that the nitrogen atom of the side chain of asparagine is bound to the reducing terminal of the sugar chain in β configuration.)

Here, when n and m are both simultaneously 0, it means that this is a sugar chain asparagine having one molecule of sugar chain and one molecule of asparagine bound together wherein no other amino acid is bound by peptide bond on either ends of the sugar chain asparagine.

Here, when n or m is 0, it means that the C-terminal carboxyl group or the N-terminal amino group of the asparagine in Formula (2a) is not bound by peptide bond to another amino acid, and is a free carboxyl group or a free amino group.

In one aspect of the present invention, n is an integer from 0 to 100, preferably an integer from 0 to 10, and more preferably an integer from 0 to 5.

In one aspect of the present invention, m is an integer from 0 to 100, preferably an integer from 0 to 10, and more preferably an integer from 0 to 5.

In one aspect of the present invention, the compound having the sugar chain asparagine structure represented by Formula (2) can be employed directly as a glycoprotein or a glycopeptide, or can be employed as those fragmented to an extent in advance by a peptide hydrolase from the glycoprotein or the glycopeptide as the source material. Alternatively, a commercially available glycopeptide or sugar chain asparagine, or derivatives thereof and the like may also be employed.

As the intermediate in the manufacturing method of the present invention, the compound represented by Formula (3) and the like can be shown:

$$\text{G-NH}_2 \tag{3}$$

(wherein G represents a sugar chain, $NH_2$ represents an amino group, and G and $NH_2$ are bound so that the nitrogen atom derived from the nitrogen atom of the side chain of said asparagine is bound to the reducing terminal of said sugar chain in β configuration.)

The compound represented by Formula (3), wherein the nitrogen atom derived from the nitrogen atom of the side chain of asparagine is bound to the reducing terminal of the sugar chain in β configuration, can also be referred to as a sugar chain amine compound.

As the activator in the manufacturing method of the present invention, the compound represented by Formula (4) can be shown:

$$\text{L}^1\text{-CO—CH}_2\text{—Y}^1 \tag{4}$$

(wherein $L^1$ is a leaving group, and $Y^1$ is an activating group.)

The compound represented by Formula (4) can also be referred to as an activator for binding the —CO—CH$_2$—$Y^1$ moiety to the nitrogen atom of the compound represented by the above Formula (3), or simply as an activator.

The manufacturing method of the present invention comprises steps (a) and (b). Steps (a) and (b) will now be described in detail below.

Step (a) can be represented as below:

(a) a step of applying a sugar chain asparagine hydrolase under basic conditions on a compound having the sugar chain asparagine structure represented by the following Formula (2):

$$\text{G-Asn} \tag{2}$$

(wherein G represents a sugar chain, Asn represents an asparagine, and G and Asn are bound so that the nitrogen atom of the side chain of said asparagine is bound to the reducing terminal of said sugar chain in β configuration) to obtain a compound represented by the following Formula (3):

$$\text{G-NH}_2 \tag{3}$$

(wherein G represents a sugar chain, $NH_2$ represents an amino group, and G and $NH_2$ are bound so that the nitrogen atom derived from the nitrogen atom of the side chain of said asparagine is bound to the reducing terminal of said sugar chain in β configuration.)

Step (a) is a step of applying a sugar chain asparagine hydrolase on a compound having the sugar chain asparagine structure represented by the above Formula (2) to obtain the compound represented by the above Formula (3) (also referred to as a sugar chain amine compound).

The sugar chain asparagine hydrolase in the manufacturing method of the present invention is not particularly limited as long as it is an enzyme that hydrolyzes the bond between the nitrogen atom in the asparagine side chain and the carbonyl carbon atom adjacent to said nitrogen atom without cleaving the bond between the reducing terminal of the sugar chain and the nitrogen atom of the asparagine side chain. A sugar chain amine compound and an aspartic add are produced from a sugar chain asparagine in this reaction.

Examples of the sugar chain asparagine hydrolase of the present invention can include a glycosylasparaginase (GA) or a peptide:N-glycanase (PNGase). For example, PNGase-F, PNGase-A, and the like depending on its origin are known as PNGases. Glycosylasparaginase (GA) or peptide:N-glycanase (PNGase) can be manufactured e.g. by a method of expressing and purifying these enzymes, or they can be obtained from BioLabs Inc. etc.

In one aspect of the present invention, when glycosylasparaginase (GA) is employed as the sugar chain asparagine hydrolase, a sugar chain asparagine in which n and m are 0 in Formula (2a) is preferably employed as the substrate.

In one aspect of the present invention, when peptide:N-glycanase (PNGase) is employed as the sugar chain asparagine hydrolase, a sugar chain asparagine-containing peptide in which n and m are not 0 in Formula (2a) is preferably employed as the substrate. When peptide:N-glycanase (PNGase) is employed, a glycopeptide called sialylglycopeptide (SGP) can be employed as the substrate.

A sialylglycopeptide (SGP) is a glycopeptide of a total of six residues wherein three amino add residues are bound on the N-terminal side of the sugar chain asparagine and two residues on the C-terminal side, and the sequence can be shown as Lys-Val-Ala-Asn(sugar chain)-Lys-Thr. A sialylglycopeptide (SGP) can be purchased from FUSHIMI Pharmaceutical Co., Ltd., or it can be manufactured by cleaving the peptide moiety from a glycoprotein or a glycopeptide having a longer peptide moiety.

In the manufacturing method of the present invention, step (a) is performed under basic conditions. Here, basic conditions refer to being basic to an extent that can realize high β selectivity in the step of obtaining a compound represented by Formula (3) (sugar chain amine compound) from a compound having the sugar chain asparagine structure represented by Formula (2). Those skilled in the art having seen the present specification will be able to recognize the extent of pH necessary to realize high β selectivity as the present invention. In one aspect of the present invention, the basic condition can be a weakly basic condition. In one aspect of the present invention, the basic condition can refer to pH 8-11, preferably pH 8-10, and more preferably pH 8-9. Such a basic condition can be realized with a solvent showing the above pH or a solvent adjusted to be at the above pH. As specific examples, common buffer solutions such as sodium hydrogen carbonate aqueous solution, sodium carbonate aqueous solution, potassium carbonate aqueous solution, and N,N-bis(2-hydroxyethyl)glycine (BICINE) buffer solution can be employed. The above basic conditions can be adjusted before the start of reaction, or may be further adjusted during reaction by pH monitoring etc. In the present invention, pH can be measured by a commonly employed pH meter (HORIBA, Ltd. pH Meter D-51S) etc. For example, sodium hydrogen carbonate aqueous solution is employed in the Examples herein, and measurement of this with the above pH meter gave a pH of about 8.5. In one embodiment of the present invention, the basic condition may be realized by e.g. a method of adding an amount of a basic substance (such as sodium hydrogen carbonate) to realize the above basic conditions to the reaction system and stirring, and does not necessarily require a step of adjusting the basic condition with a pH meter etc. as long as the above basic condition can be inevitably realized.

In one aspect of the manufacturing method of the present invention, step (a) is preferably performed under basic conditions as well as in a short period of time. Performed "in a short period of time" can mean performing in a shorter time than the ammonium carbonate method that is the conventional method. In the ammonium carbonate method that is the conventional method, it was known to ordinarily allow reaction for approximately one week. As a result of extensive investigations by the present inventors for conditions for β-selective hydrolysis reaction by a sugar chain asparagine hydrolase, it was found that by allowing the reaction condition to be basic, and further allowing the reaction time to be shorter, the ring-opening reaction of the sugar located at the reducing terminal of the sugar chain can be suppressed, and β selectivity can be further increased.

Step (a) in the manufacturing method of the present invention, under basic conditions, can efficiently yield the compound represented by Formula (3) (sugar chain amine compound) from a compound having the sugar chain asparagine structure represented by Formula (2), and can allow the reaction time to be shorter.

Here, a short period of time means a time shorter than the above conventional method, and refers to 10 minutes-3 hours, preferably 10 minutes-2 hours, and more preferably 10 minutes-1 hour. Note that continuing the reaction to the above reaction time or longer is not to be excluded from the scope of the present invention, as long as superior β selectivity in the manufacturing method of the present invention can be realized.

In one aspect of the manufacturing method of the present invention, step (a) is preferably performed under basic conditions and at a low temperature. In the ammonium carbonate method that is the conventional method, it was known to ordinarily allow reaction at 30-50° C. As a result of extensive investigations by the present inventors for conditions for hydrolysis reaction by a sugar chain asparagine hydrolase in order to obtain a sugar chain amine compound, it was found that by performing step (a) at a low temperature, the ring-opening reaction of the sugar located at the reducing terminal of the sugar chain can be suppressed, and β selectivity can be further increased.

Although approximately 37° C. is predicted to be the optimal temperature for step (a) in the manufacturing method of the present invention because it is an enzyme reaction, the present inventors, as a result of extensive investigations, surprisingly succeeded in finding experiment conditions that is superior in β selectivity as well as having sufficient reactivity by employing not only a temperature limited to approximately 37° C. which is optimal for ordinary enzymes but further a temperature intentionally lower than ordinary enzyme reactions such as 4° C.

Further, the present inventors found that even though it is anticipated for the reaction rate of the enzyme to be reduced at a low temperature, sufficient reactivity can be realized even at a low temperature and also in a short period of time such as an hour or less.

Here, a low temperature means a temperature lower than the above conventional method, and in one aspect of the present invention refers to 0° C.-40° C., preferably 0-20° C., and more preferably 0° C.-10° C. In one aspect of the present invention, the temperature is further preferably 2° C.-6° C.

The method for adjusting the temperature in order to realize a low temperature is not particularly limited as long as it is a method that can be adjusted to the above temperature. The method for adjusting the temperature can be realized by a method employed in ordinary biochemistry experiments, and can be performed with e.g. methods such as a thermostat bath and ice-cooling. In the present invention, the temperature can be measured by a commonly employed thermometer (such as a red liquid stick thermometer) and the like.

In the manufacturing method of the present invention, step (b) can be represented as below:

(b) a step of reacting the compound represented by said Formula (3) obtained in step (a) with a compound represented by the following Formula (4)

(wherein $L^1$ is a leaving group, and $Y^1$ is an activating group.)

In the manufacturing method of the present invention, step (b) is a step of reacting the compound represented by Formula (3) obtained in step (a) with the compound represented by Formula (4).

When the compound represented by Formula (3) is reacted with the compound represented by Formula (4), it is thought that the nitrogen atom of $NH_2$ in Formula (3) nucleophilically attacks the carbonyl carbon in Formula (4). It is thought that as a result, a hydrogen atom is detached from $NH_2$ in Formula (3) and $L^1$ is detached from the compound of Formula (4), and a covalent bond is formed between the nitrogen atom in Formula (3) and the carbonyl carbon in Formula (4).

This step (b) is characterized in that the configuration of the nitrogen atom bound to the reducing terminal of the sugar chain at the reducing terminal of the sugar chain is β configuration.

Here, the compound represented by Formula (4) is a compound having a leaving group $L^1$ that is detachable in step (b) and an activating group $Y^1$.

The leaving group here is not particularly limited as long as it is a leaving group that is detachable under conditions that can retain the β conformation of the sugar chain reducing terminal in step (b). In the present invention, a leaving group that is detached in a nucleophilic attack against a carbonyl carbon can be employed as the leaving group. Examples of such a leaving group include a halogen atom (such as bromine, chlorine, and iodine atoms) and the like. Moreover, for example, a symmetric acid anhydride ($Y^1$—$CH_2$—CO—O—CO—$CH_2$—$Y^1$) can also be employed as the compound represented by Formula (4), in which case the leaving group is a group represented by $Y^1$—$CH_2$—CO—O. Moreover, e.g. a hydroxysuccinimide ester can also be employed as the compound represented by Formula (4), in which case the leaving group is a hydroxysuccinimide moiety (a moiety wherein an oxygen atom is bound to the nitrogen atom of succinimide). In one aspect of the present invention, the leaving group is preferably a halogen atom or a group represented by $Y^1$—$CH_2$—CO—O, more preferably a bromine atom or a chlorine atom.

In the manufacturing method of the present invention, the activating group is not particularly limited as long as it can be employed as a reaction group for binding the compounds represented by Formula (1a) and Formula (1b) of the present invention with further other substances. In one aspect of the present invention, other substances are preferably an in vivo substance that forms a glycoconjugate in vivo. In the present invention, examples of an activating group may be a group that may react with a functional group such as a carboxyl, an amino, a hydroxyl, or a thiol group present in biological substances such as peptides or lipids, and include those where a bond is formed between the activating group and these functional groups. Moreover, in addition to groups employed in the formation of a bond described above, the activating group may be those that form a bond between the carbon atom of —$CH_2$— adjacent to the activating group and the functional group of the other substances as described above in Formula (4), wherein the activating group itself may be a substituent that is detached upon binding.

In one aspect of the manufacturing method of the present invention, the activating group employed in step (b) may be those protected by a protecting group at a portion other than the functional group moiety for reacting with the compound represented by said Formula (3). In this case, it is preferred to comprise a step of deprotecting said protecting group moiety after step (b) or in an appropriate step thereafter. For example, when a compound wherein $Y^2$ is SH is to be manufactured as the compound represented by said Formula (1a), it may be manufactured by introducing in step (b) a thioacetyl group by employing those having a thioacetyl group as $Y^2$ instead of SH in the compound represented by Formula (4), and then later deprotecting the acetyl group.

In the manufacturing method of the present invention, examples of such an activating group include a halogen atom, an amino group, a carboxyl group, a thiol group, an azide group, a hydrazino group, and a dimethoxymethyl group. In one aspect of the present invention, the activating group is preferably a bromine atom, a chlorine atom, an iodine atom, SH, $N_3$, $NHNH_2$, and $CH(OMe)_2$, and more preferably a bromine atom and an iodine atom.

Those skilled in the art having seen the present specification will be able to recognize that activating groups for the compounds described in the Examples, as well as activating groups with some degree of modification thereto can also be manufactured by the manufacturing method of the present invention.

Step (b) can be performed in a weakly basic solvent. In one aspect of the present invention, preferably a common buffer solution such as sodium hydrogen carbonate aqueous solution, sodium carbonate aqueous solution, potassium carbonate aqueous solution, and N,N-bis(2-hydroxyethyl)glycine (BICINE) buffer solution can be employed as the solvent, and more preferably sodium hydrogen carbonate aqueous solution can be employed.

The pH of step (b) is not particularly limited as long as superior 1β selectivity can be realized in step (b). In one aspect of the present invention, the pH is preferably pH 8-11, more preferably pH 8-10, and more preferably pH 8-9.

The reaction time of step (b) is not particularly limited as long as superior 1β selectivity can be realized in step (b). In one aspect of the present invention, the time is preferably 10 minutes-20 hours, more preferably 10 minutes-1 hour.

The reaction temperature of step (b) is not particularly limited as long as superior 1β selectivity can be realized in step (b). In one aspect of the present invention, the temperature is preferably 0-40° C., more preferably 0-10° C.

In one aspect of the present invention, step (b) can be completed preferably under ice-cooling or a temperature condition equivalent thereto in an hour or less.

In one aspect of the present invention, when employing the manufacturing method comprising steps (a) and (b), it is preferred that $Y^1$ is selected from the group consisting of a bromine atom, a chlorine atom, an iodine atom, SH, $N_3$, $NHNH_2$, $SHCH_2CH_2NH_2$, and $CH(OMe)_2$.

In one aspect of the present invention, when employing the manufacturing method comprising steps (a) and (b), it is preferred that $Y^1$ is selected from the group consisting of a bromine atom, a chlorine atom, an iodine atom, and $CH(OMe)_2$.

In one aspect of the present invention, the sugar chain compound having an activating group of the present invention can be synthesized by the above method of steps (a) and (b), or it can also be manufactured by a method comprising the following step (c) after the above steps (a) and (b) depending on the type of the activating group.

In other words, a method comprising steps (a)-(c) can be described as follows.

A method for manufacturing a compound represented by the following Formula (1b):

G-NH—CO—CH$_2$—Y$^2$ (1b)

(wherein G represents a sugar chain, $Y^2$ represents an activating group, and G and NH are bound so that the nitrogen atom of NH is bound to the reducing terminal of said sugar chain in β configuration)
comprising the following steps (a)-(c):

(a) a step of applying a sugar chain asparagine hydrolase under basic conditions on a compound having the sugar chain asparagine structure represented by the following Formula (2):

G-Asn (2)

(wherein G represents a sugar chain, Asn represents an asparagine, and G and Asn are bound so that the nitrogen atom of the side chain of said asparagine is bound to the reducing terminal of said sugar chain in β configuration) to obtain a compound represented by the following Formula (3):

G-NH$_2$ (3)

(wherein G represents a sugar chain, NH$_2$ represents an amino group, and G and NH$_2$ are bound so that the nitrogen atom derived from the nitrogen atom of the side chain of said asparagine is bound to the reducing terminal of said sugar chain in β configuration);

(b) a step of reacting the compound represented by said Formula (3) obtained in step (a) with a compound represented by the following Formula (5)

L$^1$-CO—CH$_2$—Z (5)

(wherein $L^1$ is a leaving group, and Z is a halogen atom); and (c) a step of reacting the compound obtained in step (b) with a compound represented by the following Formula (6a) or Formula (6b):

L$^2$-Y$^2$ (6a)

(wherein $L^2$ is a leaving group, and $Y^2$ is an activating group)

L$^3$Y$^3$ (6b)

(wherein $L^3$ is a cation, $Y^3$ is an anion of said activating group $Y^2$, and $L^3Y^3$ is a salt of $L^3$ and $Y^3$.)

In other words, the manufacturing method comprising steps (a), (b), and (c) is a reaction in which in step (b) the compound represented by Formula (3) is reacted with the compound represented by Formula (5) wherein the activating group is Z (a halogen atom) as the activator, and further as step (c), reading a compound having an activating group $Y^2$ to substitute said halogen atom with $Y^2$.

When this method is employed, a compound wherein the activating group $Y^1$ is a halogen atom in the compound represented by Formula (1a) is obtained by the reaction of step (b). If this compound was to be represented in a formula, it can be represented by the following Formula (1d):

G-NH—CO—CH$_2$—Z (1d)

(wherein G represents a sugar chain, Z represents a halogen atom, and G and NH are bound so that the nitrogen atom of NH is bound to the reducing terminal of said sugar chain in β configuration.)

Although this compound represented by Formula (1d) can also be employed as the compound of interest in the manufacturing method of the present invention, by further performing step (c) with this compound as an intermediate, the compound represented by Formula (1b) can be obtained.

In step (c), the compound obtained by step (b) is reacted with the compound represented by Formula (6a) or (6b).

Here, the compound represented by Formula (6a) is as follows:

L$^2$-Y$^2$ (6a)

(wherein $L^2$ is a leaving group, and $Y^2$ is an activating group.)

Here, $L^2$ may be a group that can be detached in step (c). In one aspect of the present invention, $L^2$ is preferably a hydrogen atom and the like. Those skilled in the art having seen the present specification will be able to appropriately investigate leaving groups other than those described in the Examples that can be similarly employed in order to introduce an activating group described herein.

Here, $Y^2$ may be an activating group among activating groups $Y^1$ previously described that can be substituted in step (c) with Z (a halogen atom) in the compound obtained by step (b). In one aspect of the present invention, $Y^2$ is preferably those having a halogen atom indicated by Z removed from the activating group $Y^1$. In one aspect of the present invention, when Z is in particular a bromine atom among halogen atoms, $Y^2$ may be a halogen atom other than a bromine atom, and is preferably those having the bromine atom removed from activating group $Y^1$.

Compounds represented by Formula (6a) include hydrazine, thioacetic add, cysteamine, and the like. Those skilled in the art having seen the present specification will be able to appropriately investigate activators other than the compounds described in the Examples that can be similarly employed in order to introduce an activating group described herein.

Here, the compound represented by Formula (6b) is as follows:

L$^3$Y$^3$ (6b)

(wherein $L^3$ is a cation, $Y^3$ is an anion of said activating group $Y^2$, and $L^3Y^3$ is a salt of $L^3$ and $Y^3$.)

In other words, when the activating group is a halogen atom etc., a salt of a halogen ion (such as chlorine, bromine, and iodine ions) and a cation can be employed as Formula (6b). Moreover, in addition to halogen atoms, a salt of an organic compound ion such as an azide ion (N3$^-$) and a cation etc. can also be used.

A cation can include an ammonium ion, an alkali metal ion (such as sodium and potassium), alkaline earth metal (such as magnesium and calcium), and the like.

Compounds represented by Formula (6b) include sodium chloride, sodium iodide, sodium azide, potassium thioacetate, and the like.

By manufacturing a compound wherein the activating group is a halogen atom such as a bromine atom by employing this manufacturing method comprising steps (a), (b), and (c), various sugar chain compounds having an activating group can be manufactured with this compound as the intermediate. There is an advantage by virtue of this method that induction into active groups having various reactivities is possible while fixing the bond between the sugar chain and the active group in β conformation. A compound wherein the activating group is a bromine atom can be advantageously employed as an intermediate because isolation is easy.

In one aspect of the present invention, when employing the manufacturing method comprising steps (a), (b), and (c), it is preferred that Z is a bromine atom, and $Y^2$ is selected from the group consisting of a chlorine atom, an iodine atom, SH, $N_3$, $NHNH_2$, and $SHCH_2CH_2NH_2$.

In one aspect of the manufacturing method of the present invention, the activating group employed in step (c) may be those protected by a protecting group at a portion other than the functional group moiety for reacting with the compound represented by said Formula (3). In this case, it is preferred to comprise a step of deprotecting said protecting group moiety after step (c) or in an appropriate step thereafter. For example, when a compound wherein $Y^2$ is SH is to be manufactured as the compound represented by said Formula (1b), it may be manufactured by introducing a thioacetyl group by employing those having a thioacetyl group as $Y^2$ instead of SH in the compound represented by Formula (6a) in step (c), and then later deprotecting the acetyl group.

Further, the present inventors after extensive investigations found that the yield can be further increased in regards to the manufacturing method of the present invention by performing the following step (d) after the above step (a) and before step (b):

(d) a step of separating said sugar chain asparagine hydrolase immobilized to a carrier from the reaction system.

Here, separating from the reaction system refers to substantially separating the reaction system and the sugar chain asparagine hydrolase. Separation does not only mean complete separation, and may be of the majority of the sugar chain asparagine hydrolase separation. Moreover, separating means removing the sugar chain asparagine hydrolase from the reaction system, but may also mean removing substances other than the sugar chain asparagine hydrolase from the reaction system, and is not restricted as long as it is a method that can substantially separate the two.

Further, the present inventors after extensive investigations found that β selectivity can be further increased in regards to the manufacturing method of the present invention by performing step (b) within a short period of time after the above step (a).

Here, within a short period of time refers to an hour or less, more preferably 10 minutes or less.

The present inventors after extensive investigations found that by binding the sugar chain asparagine hydrolase to a carrier as the method of separating the sugar chain asparagine hydrolase from the reaction system, step (d) can be facilitated, and further it becomes possible to perform step (b) within a short period of time from step (a).

In other words, in one aspect of the present invention, the sugar chain asparagine hydrolase employed is preferably immobilized to a carrier.

Immobilized to a carrier refers to immobilizing by forming a covalent bond etc. with the carrier, and the binding mode etc. is not particularly limited as long as it can be handled similarly to a carrier together with the carrier. In one aspect of the present invention, the carrier is preferably a solid phase resin. The solid phase resin employed for enzyme immobilization includes AminoLink™ Plus Coupling resin (from Thermo, agarose resin), TOYOPEARL-AF-Tresyl-650M, TOYOPEARL-AF-Formyl-650M (from Tosoh Corporation, methacrylic polymer resin), and the like, but commercially available resins can be employed regardless of the type of resin or the principle of immobilization as long as it is an immobilization carrier that can maintain enzyme activity. Moreover, as the method for immobilizing the sugar chain asparagine hydrolase to the carrier, a method of forming a covalent bond between the carrier and the enzyme, a method of forming an ion pair, a method of entrapping the enzyme, and the like can be employed. Those skilled in the art having seen the present specification will be able to investigate solid phase resins employed in the Examples of the present invention as well as similar kinds of solid phase resins.

In the manufacturing method of the present invention, by employing a sugar chain asparagine hydrolase immobilized to a carrier, the sugar chain asparagine hydrolase can be separated from the reaction system by a simple method such as filtration. The method of separating from the reaction system is not particularly limited, and e.g. filtration, centrifugation operation, and the like can be employed depending on the structure and nature of the carrier.

According to the manufacturing method of the present invention, various sugar chain compounds having an activating group can be obtained, and such sugar chain compounds can be favorably employed as a sugar chain derivative for binding in vivo substance etc. such as a peptide or a protein or a lipid to a sugar chain.

Further, the present inventors, as one aspect of the present invention, provides a novel sugar chain derivative which is a β anomer and has an activating group. As a result of extensive investigations for an activating group having favorable reactivity for binding a sugar chain to the in vivo substance etc. of interest as a sugar chain compound having an activating group, the present inventors found that at least the compound represented by Formula (1c) is particularly favorable.

In particular, the compound specifically shown as Formula (1c) in regards to the present invention was obtained after extensive investigations by the present inventors so as to have a sugar chain structure favorable as a sugar chain derivative for manufacturing a glycosylated peptide, as well as have favorable selectivity and reactivity towards a natural side chain of the peptide or a side chain introduced to the peptide.

The compound specifically shown as Formula (1c) is also a compound that can be favorably manufactured by the manufacturing method comprising steps (a) and (b) already described. The compound specifically shown as Formula (1c) is also a compound that can be favorably manufactured by the manufacturing method comprising steps (a), (b), and (c) already described.

However, the invention of the compound represented by Formula (1c) herein is not limited to those manufactured by the above manufacturing method.

Those skilled in the art having seen the present specification will recognize that in the manufacturing method of the present invention, the β selectivity of the manufacturing method of the present invention will be strongly influenced by the structure around particularly the reducing terminal, and will thus recognize that not only the compound specifically exemplified in Formula (1c) but also compounds that are slightly different in the structure of the sugar chain moiety or the structure of the activating group moiety such as those represented by Formula (1a) or Formula (1b) can be similarly manufactured by the manufacturing method of the present invention.

When the sugar chain compound having an activating group herein is employed as a derivative for binding a sugar chain to the target compound such as an in vivo substance etc., the compound represented by Formula (1c) can be of any combination of R and R' of the sugar chain of interest and a favorable activating group Y from the selection choices described in Formula (1c).

In the target compound such as an in vivo substance etc., the functional group to be the target for binding the sugar chain is not limited to the functional group that the in vivo substance etc. of interest intrinsically has in the natural state, but may also be those introduced in order to allow reaction with the sugar chain compound having an activating group of the present invention.

In the sugar chain compound having an activating group of the present invention, e.g. when the activating group is a bromine atom, a chlorine atom, an iodine atom, or SH, it can be introduced into the thiol group in the in vivo substance etc. of interest as the target. For example, when the activating group is $N_3$, it can be introduced into the alkyne group in the in vivo substance etc. of interest as the target. For example, when the activating group is $NHNH_2$, it can be introduced into the activated ester group or the aldehyde group in the in vivo substance etc. of interest as the target. For example, when the activating group is $CH(OMe)_2$, it can be introduced into the amino group in the in vivo substance etc. of interest as the target. Such relationships between the activating group and the target functional group are exemplary, and those skilled in the art having seen the present specification will be able to appropriately investigate similarly employing other functional groups that may react with the activating groups above as the target functional group.

A "sugar chain" herein includes compounds composed of two or more unit sugars (monosaccharides and/or derivatives thereof) connected together, as well as compounds composed of one unit sugar (a monosaccharide and/or a derivative thereof). Examples of such a sugar chain include, but are not limited to, a broad range such as monosaccharides and polysaccharides contained in vivo (glucose, galactose, mannose, fucose, xylose, N-acetylglucosamine, N-acetylgalactosamine, sialic add, and complexes and derivatives thereof), as well as sugar chains degraded or induced from complex biomolecules such as degraded polysaccharides, glycoproteins, proteoglycans, glycosaminoglycans, and glycolipids. When two or more unit sugars are connected together, each unit sugar is bound by a dehydration condensation by a glycoside bond in between. The sugar chain may be linear or branched.

A "sugar chain" herein also includes sugar chain derivatives, and examples of sugar chain derivatives include, are but not limited to, a sugar chain wherein the sugar that configures the sugar chain is e.g. a sugar that has a carboxyl group (such as aldonic add in which the C-1 position is oxidized to become a carboxylic add (such as D-gluconic add which is oxidized D-glucose) and uronic add in which the terminal C atom has become a carboxylic add (D-glucuronic add which is oxidized D-glucose)), a sugar that has an amino group or an amino group derivative (such as acetylated amino group) (such as N-acetyl-D-glucosamine, N-acetyl-D-galactosamine), a sugar that has both an amino group and a carboxyl group (such as N-acethylneuramic add (sialic add), N-acetylmuramic add), a deoxylated sugar (such as 2-deoxy-D-ribose), a sulfated sugar comprising a sulfate group, and a phosphorylated sugar comprising a phosphate group.

With respect to chemically synthesizing a glycoconjugate that exists in vivo (such as a glycopeptide (or a glycoprotein), a proteoglycan, and a glycolipid), the "sugar chain" herein is preferably a sugar chain that exists in vivo as a glycoconjugate (such as a glycopeptide (or a glycoprotein), a proteoglycan, and a glycolipid).

In one aspect of the present invention, with respect to chemically synthesizing a glycopeptide or a glycoprotein that exists in vivo, an N-linked sugar chain that is known to be a sugar chain bound to asparagine (also referred to as asparagine-linked sugar chain or N-form sugar chain) is preferred.

An N-linked sugar chain is a sugar chain known to be bound to the side chain of the peptide asparagine (Asn), which is known to have the pentasaccharide represented by the following formula as the basic structure.

(wherein "Man" indicates mannose, "GlcNAc" indicates N-acetylglucosamine, the left end is the non-reducing terminal, the right end is the reducing terminal, and the pentasaccharide binds to the nitrogen atom of the asparagine side chain at the reducing terminal.)

The N-linked sugar chain is known to be classified according to the structure of the sugar chain that further binds to the non-reducing terminal of the above pentasaccharide, examples of which include a high-mannose form, a complex form, or a hybrid form. In one aspect of the present invention, the sugar chain is preferably an N-linked complex-type sugar chain.

In the manufacturing method of the present invention, with respect to chemically synthesizing a pharmaceutical etc. as a glycopeptide or a glycoprotein, examples of a preferred sugar chain can include a sugar chain having identical structure (a sugar chain in which the type of constituent sugars and their binding modes are identical) to a sugar chain that exists in the human body as a glycoprotein bound to a protein (such as the sugar chain described in FEBS LETTERS, Vol. 50, No. 3, February 1975), or a sugar chain having one or more sugars deleted from the non-reducing terminal thereof.

Biantennary, triantennary, quatroantennary forms, and the like are known as complex-type sugar chains of an N-linked sugar chain, and the number of branches is not particularly limited.

In one aspect of the present invention, an example of a complex-type sugar chain of an N-linked sugar chain as a biantennary form can be the sugar chain represented by the following Formula (7).

[Chemical Formula 15]

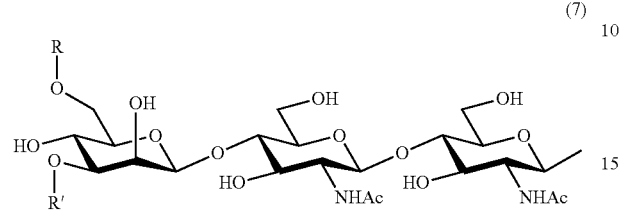

(7)

(wherein R and R' are each independently selected from the group consisting of sugar chains represented by the following Formula (8a) to Formula (8f):

[Chemical Formula 16]

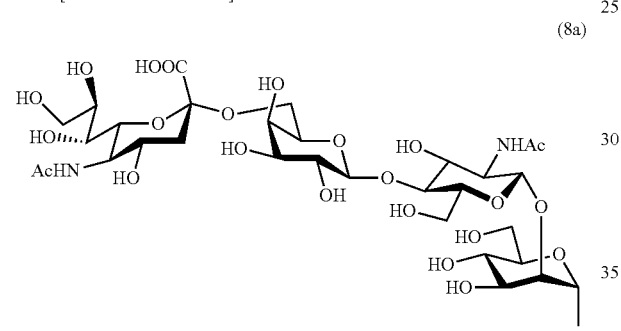

(8a)

[Chemical Formula 17]

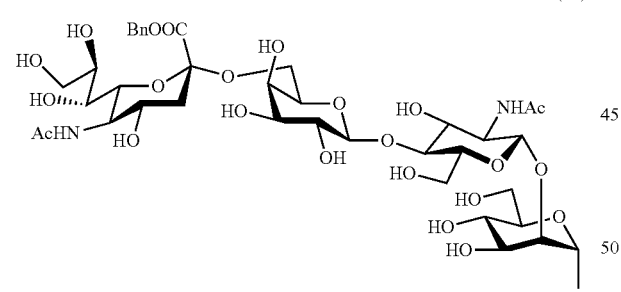

(8b)

[Chemical Formula 18]

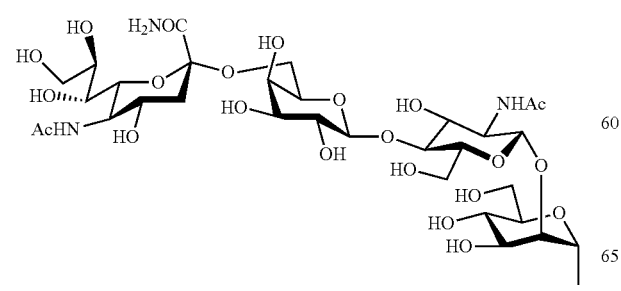

(8c)

[Chemical Formula 19]

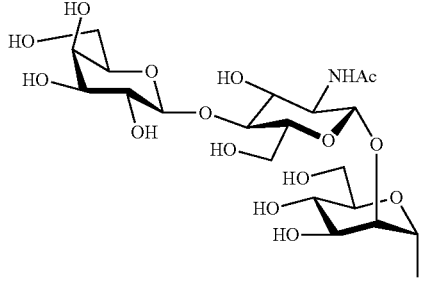

(8d)

[Chemical Formula 20]

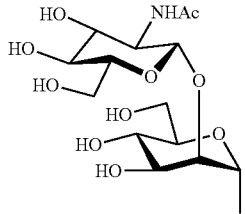

(8e)

[Chemical Formula 21]

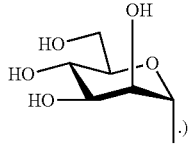

(8f)

.)

In the present invention, an N-linked sugar chain or a complex-type sugar chain includes those in which its binding mode, the presence or absence of a fucose, the presence or absence of modification to the side chain substituent, and the like are different, as long as it has the basic sugar chain skeleton commonly known as that type of sugar chain.

A disialo sugar chain herein refers to a sugar chain having the basic sugar chain structure known as an N-linked sugar chain or a biantennary complex-type sugar chain, wherein sialic adds are bound to both of the two non-reducing terminals of the biantennary form. In one aspect of the present invention, it is preferred to employ a compound in which R and R' are both a sugar chain represented by Formula (8a) in the compound of the above Formula (7) as the disialo sugar chain. In other words, if this compound was to be represented in one chemical formula, it can be represented by the following Formula (9).

[Chemical Formula 22]

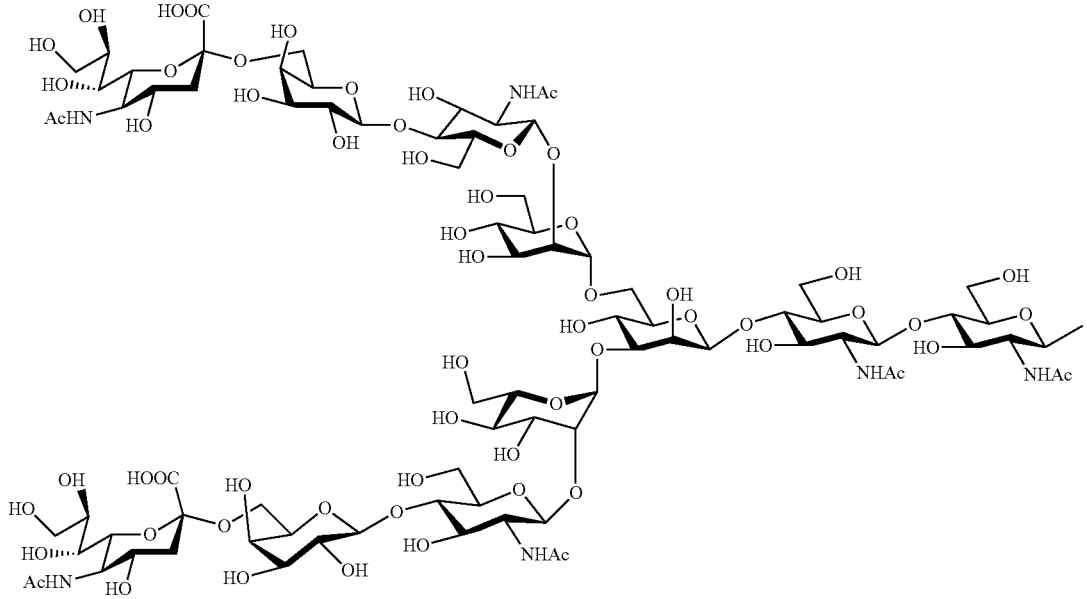

(9)

The above compound is an example of a disialo sugar chain wherein the sialic add is bound by an α2-6 bond. In one aspect of the present invention, the sugar chain represented by the following Formula (10) which is a disialo sugar chain wherein the sialic add is bound by an α2-3 bond can also be employed.

An asialo sugar chain herein refers to a sugar chain having the basic sugar chain structure known as an N-linked sugar chain or a biantennary complex-type sugar chain, which has a structure wherein sialic adds at both of the two non-reducing terminals of the biantennary form are detached from the above disialo sugar chain. In one aspect of the present invention, it is preferred to employ a compound in

[Chemical Formula 23]

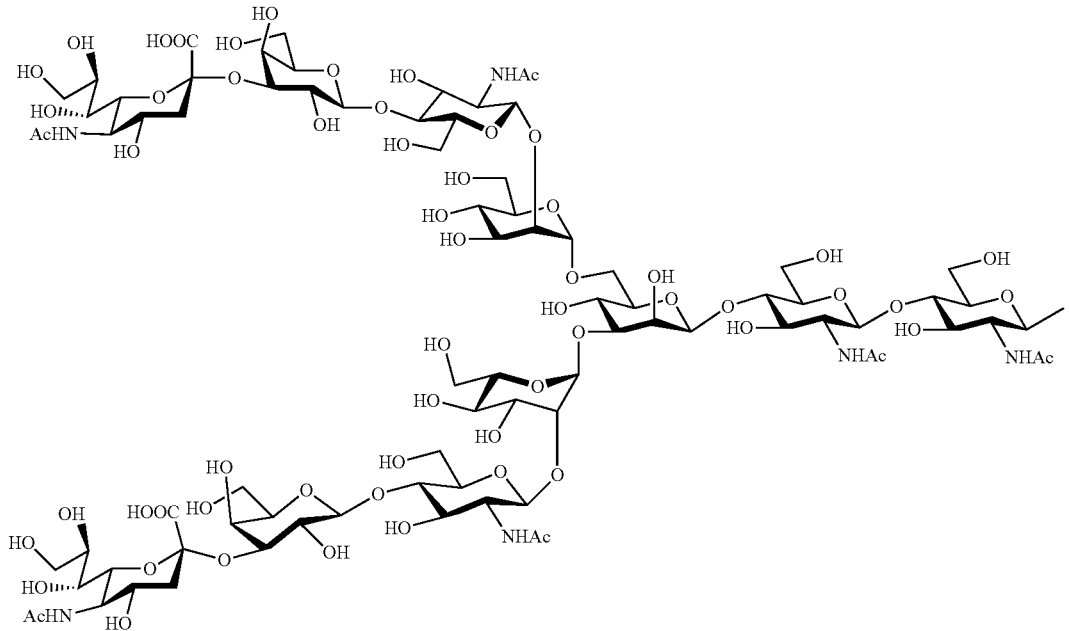

(10)

which R and R' are both a sugar chain represented by Formula (8d) in the compound of the above Formula (7) as the asialo sugar chain.

A DiGlcNAc sugar chain herein refers to a sugar chain having the basic sugar chain structure known as an N-linked sugar chain or a biantennary complex-type sugar chain, which has a structure wherein sialic adds at both of the two non-reducing terminals of the biantennary form, as well as galactose bound to the reducing terminal side of said sialic add are detached from the above disialo sugar chain. In one aspect of the present invention, it is preferred to employ a compound in which R and R' are both a sugar chain represented by Formula (8e) in the compound of the above Formula (7) as the DiGlcNAc sugar chain.

In the present invention, the sugar chain represented by Formula (7) includes the disialo sugar chain, the asialo sugar chain, and the DiGlcNAc sugar chain specifically exemplified above, as well as various sugar chains represented by independently selecting R and R'.

In one aspect of the present invention, with respect to providing the activated form of the sugar chain that plays an important role in the recognizability or the retentivity in blood and the like of the in vivo glycoprotein, the sugar chain is preferably a disialo sugar chain.

In one aspect of the present invention, since the carboxylic acid comprised in the sialic acid of the disialo sugar chain have the possibility of reacting with other substances in a step of the manufacturing method of the present invention, it is preferred that the carboxylic add of the disialo sugar chain is protected.

In one aspect of the present invention, it is preferred to esterify or amidate the carboxylic add as protection of the carboxylic add of the disialo sugar chain.

Examples of esterification include benzyl esterification, phenacyl esterification, methyl esterification, allyl esterification, and the like.

In one aspect of the present invention, an example of protecting the carboxylic add of the disialo sugar chain by esterification can include e.g. a benzyl esterified disialo sugar chain. Such a sugar chain can also be referred to herein as a dibenzyl disialo sugar chain or a diBn disialo sugar chain. A dibenzyl disialo sugar chain can be shown as a compound in which R and R' are both represented by Formula (8b) on the above Formula (7).

In one aspect of the present invention, another example of protecting the carboxylic acid of the disialo sugar chain by esterification can include e.g. a phenacyl esterified disialo sugar chain.

As an example of the method of esterifying the carboxyl group in the sialic add of the disialo sugar chain, it can be manufactured by reacting a disialo sugar chain or a derivative thereof (such as disialo sugar chain-Fmoc) with benzyl bromide or phenacyl bromide and the like. Alternatively, it can be manufactured by allowing reaction with benzyl diazomethane and the like. Methyl esterification or allyl esterification can also be manufactured according to the esterification structure of interest by methods similar to benzyl esterification or phenacyl esterification.

In one aspect of the present invention, an example of protecting the carboxylic add of the disialo sugar chain by amidation can include e.g. a compound in which R and R' are both represented by Formula (8c) in the above Formula (7) as an amidated disialo sugar chain. In one aspect of the present invention, amidation can also be a compound in which the primary amide group represented by the above Formula (8c) and the carboxylic add (the moiety shown by —COOH) of the disialo sugar chain is —CONR$^1$R$^2$ (wherein R$^1$ and R$^2$ indicates a group that may form a secondary amide group or tertiary amide group such as an alkyl group).

As an example of the method of amidating the carboxyl group in the sialic add of the disialo sugar chain, it can be manufactured by reacting a compound which is an esterified disialo sugar chain or a derivative thereof (such as disialo sugar chain-Fmoc) with ammonium hydrogen carbonate aqueous solution, aqueous ammonia, and the like. Alternatively, it can also be manufactured by e.g. a method of reacting with an organic solvent comprising a primary or secondary amine instead of the ammonium hydrogen carbonate aqueous solution and the like, and then introducing these as an amide group.

In regards to the protection of the carboxylic add of the sialic add, there have been attempts as conventional technology to employ a sugar chain having the sialic add protected by esterification and the like. However, when carrying out the amination of the reducing terminal with the conventionally employed ammonium carbonate method, it was difficult to prepare a disialo sugar chain derivative having the carboxylic add of the sialic add protected by esterification and having an activating group at the reducing terminal of the sugar chain because a portion of the ester group which is the protecting group will be subject to hydrolysis or amidation during its reaction. In contrast, according to the method of the present invention, there is a superior effect that it is possible to prepare a disialo sugar chain derivative having the carboxylic add protected by esterification because an amino form at the reducing terminal can be obtained merely by performing enzyme treatment under a low temperature in sodium hydrogen carbonate aqueous solution without going through amination by ammonium carbonate.

According to the manufacturing method of the present invention, a method for manufacturing a sugar chain derivative superior in β selectivity can be provided.

In the invention of the manufacturing method, superior in β selectivity refers to the fact that when the product of the manufacturing method is regarded as an aggregation of sugar chain compound molecules, the proportion (abundance) of β anomer against the total number of sugar chain compounds which is the sum of α and β anomers is high in terms of the configuration of the reducing terminal of the sugar chain as the product. Describing it from an opposite viewpoint, it can also be expressed as the abundance of a anomer against the total number of sugar chain compounds being small. Moreover, high abundance of β anomer can also be referred to as high purity of β anomer.

The β selectivity or the abundance of a and/or β anomer can be determined by analyzing the sugar chain compound as the product by $^1$H-NMR. For example, conditions described in the Examples herein can be employed for the analysis condition of $^1$H-NMR. Moreover, those skilled in the art will be able to appropriately investigate $^1$H-NMR analysis conditions. The β selectivity can also be determined by others such as HPLC.

In one aspect of the present invention, having high β selectivity or being superior in β selectivity refers to the fact that the α anomer abundance rate in the compound obtained by the manufacturing method is 6% or less. In one aspect of the present invention, the abundance is preferably 2% or less, and more preferably 1% or less.

In the present invention, it is preferred that the yield is also high. In one aspect of the present invention, the yield is preferably 80% or more, more preferably 90% or more.

According to the manufacturing method of the present invention, because β selectivity is high, it can also be said that the yield of the sugar chain derivative as β anomer is high.

When a sugar chain derivative was obtained in the conventional method by a manufacturing method with low β selectivity, if α and β anomers could be separated and purified, it was also conceivable to separate and purify only the β anomer. However, according to the method the present invention, a sugar chain derivative which is a β anomer can be manufactured at a better yield than the method of comprising such a separation and purification step.

Further, when separation and purification of α and β anomers of the sugar chain compound are difficult, a sugar chain derivative with extremely high β anomer rate can be manufactured according to the present invention.

When employing the sugar chain compound having an activating group of the present invention as an intermediate that is a sugar chain derivative for reacting with an in vivo substance, i.e. as an intermediate composition that is an aggregate of multiple molecules for manufacturing a glycoconjugate, it can be obtained as a composition that has uniform sugar chain structure and with extremely high β anomer rate if manufactured with the manufacturing method of the present invention. Here, in an aggregate of multiple molecules, sugar chain structure is uniform refers to the fact that the type of each sugar configuring the sugar chain, the binding order, and the binding mode between sugars are identical when compared between sugar chain derivatives, and refers to the fact that at least 90% or more, preferably 95% or more, and more preferably 99% or more of the sugar chain structure is uniform. Moreover, extremely high β anomer rate refers to the fact that the β anomer abundance rate is 94% or higher, preferably 99% or higher. A sugar chain derivative having uniform sugar chain and with extremely high β anomer rate has constant quality, and is preferred particularly in fields such as pharmaceuticals manufacture or assays.

An aspect of the present invention disclosed herein as exemplification may be carried out even if a configuration element not clearly disclosed herein does not exist.

All patents and other publications specified herein are expressly cited herein by reference in their entireties. These documents are provided solely for the purpose of disclosing related technology preceding the filing date of the present application, and are not to be construed as an admission by the present inventors that the present invention does not hold the right to precede said disclosures due to prior inventions or for any other reasons. The dates related to the contents of these documents and all descriptions related to indications are based on information available to the applicants, and do not configure in any way an admission that the dates and contents of these documents are accurate.

The terms used herein are employed for describing particular embodiments, and do not intend to limit the invention.

The terms "containing" or "comprising" as used herein, unless the content clearly indicates to be understood otherwise, intends the presence of the described items (such as components, steps, elements, or numbers), and does not exclude the presence of other items (such as components, steps, elements, or numbers). When the existence of said other items (such as components, steps, elements, or numbers) may be excluded, the term "consist of" may be applied. The concept of terms "containing" or "comprising" encompasses the concept of the term "consist of."

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

The embodiments of the present invention may be described with reference to schematic diagrams. In such a case, they may be exaggerated in presentation in order to allow clear description.

Terms such as first and second are employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The numeric values employed herein for indicating component content or numeric value range and the like, unless explicitly indicated, are to be understood as being modified by the term "about" For example, "30 mL," unless explicitly indicated, is to be understood to mean "about 30 mL."

Unless clearly indicated to mean otherwise in context, when used in the specification and claims herein, it should be recognized that each aspect represented in singular form may also be a plural form as long as it is not technically contradicting, and vice versa.

All of the disclosures of the literatures cited herein should be deemed as cited herein, and those skilled in the art will cite and recognize the related disclosed contents in these prior art literatures as a part of the present specification according to the context herein without departing from the spirit and scope of the present invention.

The present invention will now be described in further detail with reference to Examples. However, the present invention can be embodied by various aspects, and shall not be construed as being limited to the Examples described herein. Those skilled in the arts of related fields will be able to carry out the present invention with various modifications, additions, deletions, substitution, and the like without altering the spirit or scope of the present invention.

EXAMPLES

In the following Examples, the "disialo sugar chain" compound employed was the following Formula (7):

[Chemical Formula 24]

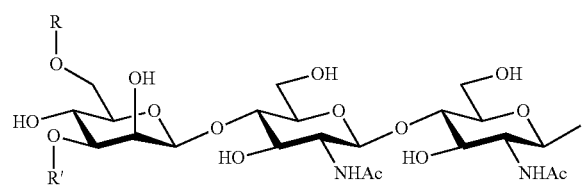

(7)

in which R and R' are both the sugar chain represented by the following Formula (8a):

[Chemical Formula 25]

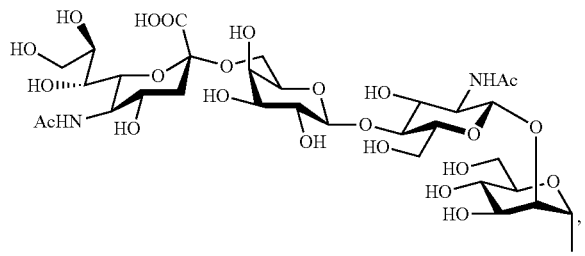

(8a)

the "asialo sugar chain" compound employed was the above Formula (7) in which R and R' are both the sugar chain represented by the following Formula (8d):

[Chemical Formula 26]

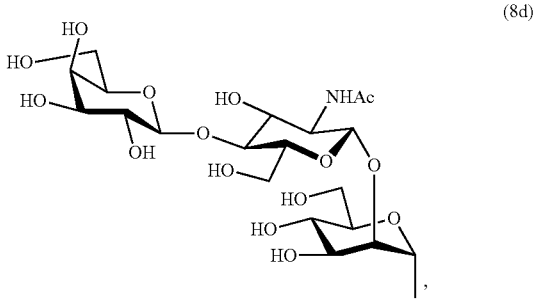

(8d)

and the "DiGlcNAc sugar chain" compound employed was the above Formula (7) in which R and R' are both the sugar chain represented by the following Formula (8e):

[Chemical Formula 27]

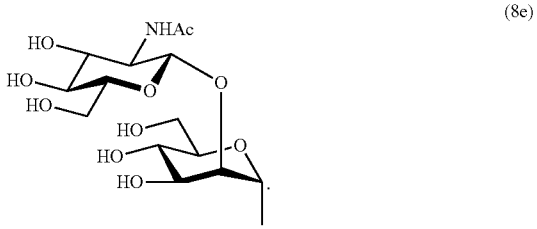

(8e)

Note that those skilled in the art having seen the present specification will be able to recognize that in addition to cases where these sugar chains are employed, manufacture is also possible when other sugar chains of the present invention are employed similarly to the Examples below by applying appropriate investigations as necessary. Moreover, in the Examples below, "—NH-AC-" means "—NH—CO—CH$_2$—."

REFERENCE EXAMPLES (Reference Example 1) Synthesis of Disialo Sugar Chain Asparagine Mixture To ethanol (EtOH, 67 mL) under stirring was placed one egg yolk. After stirring for about 5 hours, this was filtered, and further washed with EtOH (30 mL). To the crystals obtained was again added EtOH (83 mL), this was stirred overnight, and then filtered, and subsequently washed with EtOH (30 mL). Subsequently, the crystals were dried to obtain about 3 g of delipidated egg yolk.

After dissolving the delipidated egg yolk obtained in phosphate buffer (pH=7.0, 30 mL), NaN$_3$ (10 mg) was added. Further, orientase ONS (from HBI, 1.0 g) was added, and left at 50° C. for about 24 hours. After confirmation of the completion of the reaction with thin layer chromatography (TLC), the reaction solution was filtered with Celite (Celite Corporation). The amount of the filtrate was reduced by concentration, and then purified with gel filtration column chromatography (Sephadex G-25, 2.5×100 cm, water). The fraction comprising the sugar of interest was collected and concentrated, and subsequently lyophilized.

To the residue obtained (about 430 mg) were added Tris-HCl.calcium chloride buffer solution (pH=7.5, 43 mL) and sodium azide (NaN$_3$, 21 mg) to dissolve said residue. Further, Actinase E (43 mg) was added, and left for 24 hours with pH check every 12 hours. After allowing it to stand for 24 hours left, to the reaction solution was again added Actinase E (21.5 mg), and allowed to react again for about 48 hours with pH check. After confirmation of the completion of the reaction with TLC, this was subjected to celite filtration. The filtrate was reduced by concentration, and then purified with gel filtration column chromatography (Sephadex G-25, 2.5×100 cm, water). The fraction comprising the disialo sugar chain asparagine of interest was collected and concentrated, and subsequently lyophilized to obtain a mixture comprising disialo sugar chain asparagine.

(Reference Example 2) Synthesis of Disialo Sugar Chain Asparagine-Fmoc Wherein Amino Group Nitrogen of Asparagine is Protected with Fmoc Group The disialo sugar chain asparagine mixture obtained in Reference Example 1 (about 120 mg) was dissolved in water (1.5 mL), and sodium hydrogen carbonate (26 mg) was added. Further, Fmoc-Osu[N-(9-Fluorenylmethyloxycarbonyl)oxysuccinimide] (68 mg) dissolved in dimethylformamide (DMF, 2.5 mL) was added, and then this was allowed to react at room temperature for 2 hours. After confirmation of the disappearance of the source material with TLC, this was concentrated with an evaporator. To the residues were added water (15 mL) and diethyl ether (25 mL), and stirred for 10 minutes. Subsequently, after liquid separation, the aqueous layer was washed with diethyl ether (15 mL), and further concentrated and lyophilized. Subsequently, the residue obtained was purified on a gradient with an ODS column (Wakogel 100C18). The fraction comprising the sugar chain was collected, concentrated, and then lyophilized. The residue obtained was purified with an HPLC preparative column (YMC-Pack R&D ODS, D-ODS-5-A 20×250 mm, AN/25 mM AcONH$_4$ buffer=20/80, 7.5 ml/min). The main peak coming out after about 15 minutes was aliquoted, and then concentrated. Subsequently, desalting treatment was performed with the ODS column. After lyophilization, about 13.3 mg of the disialo sugar chain asparagine-Fmoc of interest which is a sugar chain asparagine compound wherein the amino group nitrogen of asparagine is protected with an Fmoc group was obtained.

(Reference Example 3) Synthesis of Disialo Sugar Chain Asparagine-Fmoc Wherein Carboxylic Acid in Sialic Add is Benzyl Esterified Cold aqueous solution of the disialo sugar chain asparagine-Fmoc obtained in Reference Example 2 (20 mg, 7.8

μmol) was flowed through Dowex-50W×8 (H+) column (φ 0.5 cm×5 cm) chilled to 4° C., and the eluted aqueous solution was lyophilized.

The disialo sugar chain asparagine-Fmoc obtained was dissolved in ice water at 4° C., to this was added $Cs_2CO_3$ aqueous solution (2.5 mg/1 mL), and the pH of the aqueous solution was adjusted to 5-6. This sugar chain aqueous solution was then lyophilized. The disialo sugar chain asparagine-Fmoc sample after lyophilization was dissolved in dry DMF (1.3 mL), benzyl bromide (5.1 μL) was added, and stirred under argon flow at room temperature for 45 hours. After confirmation of the completion of the reaction with TLC, the reaction solution was added to diethyl ether (10 mL) cooled to 0° C. to allow precipitation of the substance of interest. This was filtered with a paper filter. To the remaining substance of interest was added distilled water, this was eluted as a filtrate, and then concentrated under reduced pressure. The residue obtained was purified on an ODS column to obtain disialo sugar chain asparagine-Fmoc wherein the carboxylic add in the sialic add is benzyl esterified (182 mg, 6.6 μmol and a yield percent of 85%) as the compound of interest.

(Reference Example 4) Synthesis of Disialo Sugar Chain Asparagine-Fmoc Wherein Carboxylic Acid in Sialic Add is Protected with Phenacyl Ester Group The disialo sugar chain asparagine-Fmoc obtained in Reference Example 2 (153 mg, 59.8 μmol) was dissolved in DMF (1.9 mL), and to this were added LiBr (51.9 mg, 598.0 μmol) and phenacyl bromide (119.0 mg, 598.0 μmol), and stirred at 37° C. for 18 hours. After confirming the completion of the reaction with HPLC, the reaction solution was added in toluene (20 mL) to precipitate the sugar chain component as a slurry. This slurry was centrifuged by a centrifugal separator, and the residue comprising the sugar chain of interest was collected. The residue collected was purified on an ODS column to obtain disialo sugar chain asparagine-Fmoc wherein the carboxylic add in the sialic add is phenacyl esterified (100.4 mg, 35.9 μmol and a yield percent of 60%) as the compound of interest.

(Reference Example 5) Preparation of Immobilized GA Enzyme

The region encoding glycosylasparaginase (GA) was obtained by PCR from the genome DNA of a Gram-negative bacillus *Elizabethkingia meningoseptica*. A His×6 tag gene was added to the C-terminal of the GA gene in order to facilitate the purification of GA enzyme, a protein expression vector pET24a (Novagen) was employed to construct a C-terminal His tag-fused GA expression vector. The host E constrain Rosetta2 (DE3)pLysS (Novagen) was transformed by the C-terminal His tag-fused GA expression vector. This bacteria was cultured with 2×YT medium to allow expression of the protein of interest as a bacterial soluble protein. The bacterial cell was ultrasonically homogenized to elute the protein of interest, and the protein of interest was purified with an $Ni^{2+}$ column (GE Healthcare).

The protein solution after purification (100 mL, protein concentration: 17.5 mg/mL, specific activity: 69.6 units/mL) was added to a solid phase resin (TOYOPEARL AF-Tresyl, 30 g) washed with 0.1 M phosphate buffer (pH=7.4) in advance, and stirred at 20° C. for 4 hours. After 4 hours, this was filtered, and the collected solid phase resin was washed with 1 M NaCl. In order to cap the remaining active group on the solid phase resin, 0.5 M NaCl and 0.5 M Tris-HCl buffer (pH=7.4, 200 mL) were added and stirred at 20° C. for 1 hour. After 1 hour, this was filtered, the collected solid phase resin was washed with 1 M NaCl aqueous solution and subsequently with water to obtain a solid phase resin having GA enzyme immobilized on the resin surface (immobilized GA enzyme-containing solid phase resin, hereinafter also referred to as immobilized GA enzyme) (120 mL, specific activity 5.8 units/mL).

EXAMPLES (Example 1) Synthesis of Disialo Sugar Chain-NH—AcBr Wherein Carboxylic Add in Sialic Add is Benzyl Esterified, when Step (a) is Performed Under Temperature Condition of 37° C.

The disialo sugar chain asparagine-Fmoc wherein the carboxylic add in the sialic add is benzyl esterified obtained in Reference Example 3 (1.0 g, 0.4 mmol) was dissolved in dimethylformamide (DMF) (10.0 mL), and then piperidine (1442 μL, 1.5 mmol) was added, and allowed to react at room temperature. After 30 minutes, the completion of the reaction was confirmed by the disappearance of the source material peak eluting at 20 minutes and the confirmation of a new peak eluting at β minutes in HPLC analysis (analysis condition (1) below). Here, the compound confirmed as the new peak was thought to be disialo sugar chain asparagine wherein the carboxylic add in the sialic add is benzyl esterified. After confirmation of the completion of the reaction, the reaction solution was added to dichloromethane (DCM, 50 mL) to precipitate the sugar chain compound. 4.6% bromoacetic add aqueous solution (10 mL) was added in order to dissolve the sugar chain compound precipitated in DCM, DCM was removed by partitioning, the aqueous phase was washed with DCM, and then collected. To the collected aqueous phase were added $NaHCO_3$ (874.0 mg) and the immobilized GA enzyme prepared in Reference Example 5 (about 10 mL), and stirred under a temperature condition of 37° C. One hour after the start of reaction, after confirming the completion of the reaction by the disappearance of the source material peak eluting at 14 minutes and the confirmation of a new peak eluting at 16 minutes in HPLC analysis (analysis condition (2)), the immobilized enzyme was removed by filtration. Here, the compound confirmed as the new peak was thought to be disialo sugar chain-$NH_2$ wherein the carboxylic add in the sialic add is benzyl esterified. After adding $NaHCO_3$ (537.6 mg, 6.4 mmol) to the filtrate obtained, bromoacetyl bromide (1.1 mL, 12.7 mmol) dissolved in acetonitrile (10 mL) was added, and stirred under ice-cooling. The completion of the reaction was confirmed by the disappearance of the source material peak eluting at 16 minutes and the confirmation of a new peak eluting at 27 minutes in HPLC analysis (analysis condition (2)). This reaction with bromoacetyl bromide was completed in an hour or less. Here, the compound confirmed as the new peak was thought to be disialo sugar chain-NH—AcBr wherein the carboxylic add in the sialic add is benzyl esterified. After confirmation of the completion of the reaction, the reaction solution was diluted with 5% HBr aqueous solution (30 mL), and purified with an ODS carrier (Nacalaitesque, ODS-140C18OPN, solvents are substituted in the order of water, 5% acetonitrile aqueous solution, and 50% acetonitrile aqueous solution in order to elute the sugar chain) to obtain benzyl esterified disialo sugar chain bromoacetamide at a yield amount of 816.0 mg and a yield percent of 89%. As a result of analyzing the sugar chain obtained, the α isomer abundance ratio was 5.1%. The α isomer abundance ratio was analyzed with $^1$H-NMR under the following $^1$H-NMR conditions and calculated by the area percentage in $^1$H-NMR. In the Examples and Comparative Examples, the analysis method of the α isomer abundance ratio is hereinafter similar.

HPLC analysis condition (1): (UG-120 250×4.6 mm, developing solvent A: 25 mM ammonia acetate aqueous solution, B: acetonitrile, gradient: A 90% 0.70 mL/min→A 40% 0.70 ml/min, 30 minutes)

HPLC analysis condition (2): (UG-120 250×4.6 mm, developing solvent: 25 mM ammonia acetate aqueous solution:acetonitrile=86:14, 0.70 ml/min, 0.70 ml/min)

$^1$H-NMR (400 MHz, D$_2$O, external standard: acetone ($^1$H: 2.61 ppm)

δ 7.42 (m, 10H, Ar), 5.68 (d, GlcNAc1-H-1 (α isomer)), 5.31 (d, 1H, Bn-CH$_2$), 5.24 (d, 1H, Bn-CH$_2$), 5.05 (s, 1H, Man4-H-1), 5.00 (d, 1H, GlcNAc1-H-1 (β isomer)), 4.87 (s, 1H, Man4'-H-1), 4.53 (m, 3H, GlcNAc2,5,5'-H-1), 4.26 (d, 2H, Gal6,6'-H-1), 4.18 (bs, 1H, Man3-H-2), 4.12 (bd, 1H, Man4-H-2), 4.04 (bd, 1H, Man4'-H-2), 2.61 (m, 2H, NeuAc7,7'-H-3 eq), 2.01, 1.97, 1.95, 1.94 (m, 18H, Ac×6), 1.77 (dd, 2H, NeuAc7,7'-H-3 ax)

MALDI-MS: Calcd for C$_{100}$H$_{152}$BrN$_7$O$_{62}$ [M+Na]$^+$ 2544.804, found 2544.470.

(Example 2) Synthesis of Disialo Sugar Chain-NH—AcBr Wherein Carboxylic Acid of Sialic Add is Benzyl Esterified, when Step (a) is Performed Under Temperature Condition of 4° C. or Below The disialo sugar chain asparagine-Fmoc obtained wherein the carboxylic add in the sialic add is benzyl esterified obtained in Reference Example 3 (29.8 g, 10.9 mmol) was dissolved in dimethylformamide (DMF, 297.5 mL), piperidine (4.3 mL, 43.4 mmol) was added, and allowed to react at room temperature. After 30 minutes, the completion of the reaction was confirmed by the disappearance of the source material peak eluting at 20 minutes and the confirmation of a new peak eluting at β minutes in HPLC analysis (analysis condition (1)). Here, the compound confirmed as the new peak was thought to be disialo sugar chain asparagine wherein the carboxylic add in the sialic add is benzyl esterified. After confirmation of the completion of the reaction, the reaction solution was added to DCM (900 mL) to precipitate the sugar chain. 4.6% bromoacetic add aqueous solution (312 mL) was added in order to dissolve the sugar chain precipitated in DCM, DCM was removed by partitioning, the aqueous phase was washed with DCM, and then collected. To the collected aqueous phase was added NaHCO$_3$ (26.0 g) and cooled for 1 hour at 4° C. After 1 hour, immobilized GA enzyme (about 100 mL) was added and stirred under a temperature condition of 4° C. One hour after the start of reaction, after confirming the completion of the reaction by the disappearance of the source material peak eluting at 14 minutes and the confirmation of a new peak eluting at 16 minutes in HPLC analysis (analysis condition (2)), the immobilized enzyme was removed by filtration. Here, the compound confirmed as the new peak was thought to be disialo sugar chain-NH$_2$ wherein the carboxylic add in the sialic add is benzyl esterified. After adding NaHCO$_3$ (63.8 g, 760.0 mmol) to the filtrate obtained, bromoacetyl bromide (32.9 mL, 380.0 mmol) dissolved in acetonitrile (110 mL) was added, and stirred under ice-cooling. The completion of the reaction was confirmed by the disappearance of the source material peak eluting at 16 minutes and the confirmation of a new peak eluting at 27 minutes in HPLC analysis (analysis condition (2)). This reaction with bromoacetyl bromide was completed in an hour or less. Here, the compound confirmed as the new peak was thought to be disialo sugar chain-NH—AcBr wherein the carboxylic add in the sialic acid is benzyl esterified. After confirmation of the completion of the reaction, the reaction solution was diluted with 5% HBr aqueous solution (450 mL), and purified with an ODS carrier (Nacalaitesque, ODS-140C18OPN, solvents are substituted in the order of water, 5% acetonitrile aqueous solution, and 50% acetonitrile aqueous solution in order to elute the sugar chain) to obtain benzyl esterified disialo sugar chain bromoacetamide (hereinafter also referred to as "diBn disialo sugar chain-NH—AcBr") at a yield amount of 26.6 g and a yield percent of 97%. As a result of analyzing the sugar chain obtained, the α isomer abundance ratio thereof was 0.8% or less (in all cases when experimented with n=2).

HPLC analysis condition (1): (UG-120 250×4.6 mm, developing solvent A: 25 mM ammonia acetate aqueous solution, B: acetonitrile, gradient: A 90% 0.70 ml/min→A 40% 0.70 ml/min, 30 minutes)

HPLC analysis condition (2): (UG-120 250×4.6 mm, developing solvent: 25 mM ammonia acetate aqueous solution:acetonitrile=86:14, 0.70 ml/min, 0.70 ml/min)

$^1$H-NMR (400 MHz, D$_2$O, external standard: acetone ($^1$H: 2.61 ppm)

δ 7.39 (m, 10H, Ar), 5.29 (d, 1H, Bn-CH$_2$), 5.22 (d, 1H, Bn-CH$_2$), 5.03 (s, 1H, Man4-H-1), 4.98 (d, 1H, GlcNAc1-H-1), 4.84 (s, 1H, Man4'-H-1), 4.68 (s, 1H, Man3-H-1), 4.51 (m, 3H, GlcNAc2,5,5'-H-1), 424 (d, 2H, Gal6,6'-H-1), 4.16 (bs, 1H, Man3-H-2), 4.10 (bd, 1H, Man4-H-2), 4.02 (bd, 1H, Man4'-H-2), 2.59 (m, 2H, NeuAc7,7'-H-3 eq), 1.98, 1.95, 1.92, 1.91 (m, 18H, Ac×6), 1.75 (dd, 2H, NeuAc7,7'-H-3 ax)

MALDI-MS: Calcd for C$_{100}$H$_{152}$BrN$_7$O$_{62}$ [M+Na]$^+$ 2544.804, found 2545.509.

(Example 3) Synthesis of Disialo Sugar Chain Asparagine

The disialo sugar chain asparagine-Fmoc obtained in Reference Example 2 (15.5 g, 6.1 mmol) was dissolved in water (100 mL), 25% ammonia water (125 mL) was added, and stirred at 37° C. After 4 hours, the completion of the reaction was confirmed by the disappearance of the source material peak eluting at 7 minutes in HPLC analysis. After confirmation of the completion of the reaction, the insoluble matter produced during the reaction was removed by filtration, and disialo sugar chain asparagine was obtained at a yield amount of 14.1 g and a yield percent of 99% by lyophilizing the filtrate.

HPLC analysis condition: (UG-120 (250×4.6 mm), developing solvent: 25 mM ammonia acetate aqueous solution: acetonitrile=80:20, 0.70 ml/min)

$^1$H-NMR (400 MHz, D$_2$O, external standard: acetone ($^1$H: 2.61 ppm)

δ 5.04 (s, 1H, Man4-H-1), 4.98 (d, 1H, GlcNAc1-H-1), 4.86 (s, 1H, Man4'-H-1), 4.52 (m, 3H, GlcNAc2,5,5'-H-1), 4.35 (d, 2H, Gal6,6'-H-1), 4.16 (bs, 1H, Man3-H-2), 4.10 (bd, 1H, Man4-H-2), 4.03 (bd, 1H, Man4'-H-2), 2.83 (dd, 1H, Asn(CH$_2$)), 2.74 (dd, 1H, Asn(CH$_2$)), 2.58 (bdd, 2H, NeuAc7,7'-H-3 eq), 1.99, 1.98, 1.97, 1.94, 1.92 (m, 12H, Ac×3), 1.63 (dd, 2H, NeuAc7,7'-H-3 ax) MALDI-MS: Calcd for C$_{88}$H$_{141}$BrN$_8$Na$_3$O$_{64}$[M+Na]$^+$2425.762, found 2425.480.

(Example 4) Synthesis of Disialo Sugar Chain-NH—AcBr

The disialo sugar chain asparagine synthesized in Example 3 (0.9 g, 0.4 mmol) was dissolved in 1 M NaHCO$_3$ aqueous solution (10 mL), and cooled for 1 hour at 4° C. After 1 hour, immobilized GA enzyme (about 4 mL) was added and stirred under a temperature condition of 4° C. One hour after the start of reaction, after confirming the completion of the reaction by the disappearance of the source material peak eluting at β minutes and the confirmation of a new peak eluting at 16 minutes in HPLC analysis, the immobilized enzyme was removed by filtration. Here, the compound confirmed as the new peak was thought to be disialo sugar chain-NH$_2$. After adding NaHCO$_3$ (3.1 g, 37.0 mmol) to the filtrate obtained, bromoacetyl bromide (1.6 mL, 18.5 mmol) dissolved in dichloromethane (DCM, 5.6 mL) was added, and stirred under ice-cooling. The reaction was confirmed complete by the disappearance of the source material peak eluting at 16 minutes and the confirmation of a new peak eluting at 20 minutes in HPLC analysis. This reaction with bromoacetyl bromide was completed in an hour or less. Here, the compound confirmed as the new peak was thought to be disialo sugar chain-NH—AcBr. Subsequently, the DCM phase was removed by partitioning, and the aqueous phase was purified with gel filtration column chromatography (Sephadex G25, 2.3 cm×100 cm, water, flow rate 1.0 ml/min). The fraction comprising the sugar chain was concentrated, and then lyophilized to obtain disialo sugar chain bromoacetamide (disialo sugar chain-NH—AcBr) at a yield amount of 0.4 g and a yield percent of 46%. As a result of analyzing the sugar chain obtained, the α isomer abundance ratio thereof was 02%.

$^1$H-NMR (400 MHz, D$_2$O, external standard: acetone ($^1$H: 2.61 ppm)

δ 5.04 (s, 1H, Man4-H-1), 4.98 (d, 1H, GlcNAc1-H-1), 4.85 (s, 1H, Man4'-H-1), 4.52 (m, 3H, GlcNAc2,5,5'-H-1), 4.35 (d, 2H, Gal6,6'-H-1), 4.16 (bs, 1H, Man3-H-2), 4.10 (bd, 1H, Man4-H-2), 4.02 (bd, 1H, Man4'-H-2), 2.57 (bdd, 2H, NeuAc7,7'-H-3 eq), 1.99, 1.98, 1.93, 1.91 (m, 12H, Ac×3), 1.65 (dd, 2H, NeuAc7,7'-H-3 ax)

MALDI-MS: Calcd for C$_{66}$H$_{138}$BrN$_7$Na$_2$O$_{62}$ [M+Na]$^+$ 2408.674, found 2408.620.

(Example 5) Synthesis of Asialo Sugar Chain Asparagine

Asialo sugar chain asparagine-Fmoc (from Glytech. Inc., 72 g, 3.6 mmol) was dissolved in water (36 mL), 25% ammonia water (60 mL) was added, and stirred at 37° C. After 4 hours, the completion of the reaction was confirmed by the disappearance of the source material peak eluting at 12 minutes in HPLC analysis. After confirmation of the completion of the reaction, the insoluble matter produced during the reaction was removed by filtration, and an asialo sugar chain asparagine was obtained at a yield amount of 62 g and a yield percent of 97% by lyophilizing the filtrate.

HPLC analysis condition: (Kromasil (250×4.6 mm), developing solvent: 25 mM ammonia acetate aqueous solution:acetonitrile=80:20, 0.70 ml/min)

$^1$H-NMR (400 MHz, D$_2$O, external standard: acetone ($^1$H: 2.61 ppm)

δ 5.04 (s, 1H, Man4-H-1), 4.99 (d, 1H, GlcNAc1-H-1), 4.84 (s, 1H, Man4'-H-1), 4.52 (m, 3H, GlcNAc2,5,5'-H-1), 4.39 (d, 2H, Gal6,6'-H-1), 4.17 (bs, 1H, Man3-H-2), 4.11 (bd, 1H, Man4-H-2), 4.03 (bd, 1H, Man4'-H-2), 2.81 (dd, 1H, Asn(CH$_2$)), 2.70 (dd, 1H, Asn(CH$_2$)), 2.00, 1.97, 1.96, 1.93 (m, 12H, Ac×3)

MALDI-MS: Calcd for C$_{66}$H$_{110}$N$_6$O$_{48}$ [M+Na]$^+$ 1777.625, found 1777.675.

(Example 6) Synthesis of Asialo Sugar Chain-NH—AcBr

The asialo sugar chain asparagine synthesized in Example 5 (2.5 g, 1.4 mmol) was dissolved in 0.5 M NaHCO$_3$ aqueous solution (31.5 mL), and cooled for 1 hour at 4° C. After 1 hour, immobilized GA enzyme (about 12 mL) was added, and stirred at 4° C. One hour after the start of reaction, after confirming the completion of the reaction by the disappearance of the source material peak eluting at β minutes and the confirmation of a new peak eluting at 21 minutes in HPLC analysis, the immobilized enzyme was removed by filtration. After adding NaHCO$_3$ (8.5 g, 98.0 mmol) to the filtrate obtained, bromoacetyl bromide (4.4 mL, 49.0 mmol) dissolved in DCM (16.7 mL) was added, and stirred under ice-cooling. The completion of the reaction was confirmed by the disappearance of the source material peak eluting at 21 minutes and the confirmation of a new peak eluting at 24 minutes in HPLC analysis. This reaction with bromoacetyl bromide was completed in an hour or less. After confirmation of the completion of the reaction, the DCM phase was removed by partitioning, and the aqueous phase was puled with gel filtration column chromatography (Sephadex G25, 2.3 cm×100 cm, water, flow rate 1.0 ml/min). The fraction comprising the sugar chain was concentrated and lyophilized to obtain asialo sugar chain bromoacetamide (asialo sugar chain-NH—AcBr) at a yield amount of 2.0 g and a yield percent of 80%. As a result of analyzing the sugar chain obtained, the α isomer abundance ratio thereof was 1.0%. This $^1$H-NMR spectrum is shown in FIG. 4. As shown in FIG. 4, according to the method of the present invention, other than the main product β anomer, signals of impurities etc. derived from the source material were nearly all undetected.

HPLC analysis condition: (Hydrosphere 250×4.6 mm, developing solvent A: 25 mM ammonia acetate aqueous solution, B: acetonitrile, gradient: A 100% 0.70 ml/min→A 90% 0.70 ml/min, 30 minutes)

$^1$H-NMR (400 MHz, D$_2$O, external standard: acetone ($^1$H: 2.61 ppm)

δ 5.03 (s, 1H, Man4-H-1), 4.97 (d, 1H, GlcNAc1-H-1), 4.84 (s, 1H, Man4'-H-1), 4.51 (m, 3H, GlcNAc2,5,5'-H-1), 4.38 (d, 2H, Gal6,6'-H-1), 4.17 (bs, 1H, Man3-H-2), 4.11 (bd, 1H, Man4-H-2), 4.03 (bd, 1H, Man4'-H-2), 1.99, 1.97, 1.96, 1.92 (m, 18H, Ac×6)

MALDI-MS: Calcd for C$_{64}$H$_{106}$BrN$_5$O$_{46}$ [M+Na]$^+$ 1782.519, found 1782.462.

(Example 7) Synthesis of DiGlcNAc Sugar Chain Asparagine

DiGlcNAc sugar chain asparagine-Fmoc (from Glytech. Inc., 1.0 g, 0.6 mmol) was dissolved in water (5.1 mL), 25% ammonia water (8.5 mL) was added, and stirred at 37° C. After 4 hours, the completion of the reaction was confirmed by the disappearance of the source material peak eluting at 17 minutes in HPLC analysis. After confirmation of the completion of the reaction, the insoluble matter produced during the reaction was removed by filtration, and a DiGlcNAc sugar chain asparagine was obtained at a yield amount of 0.8 g and a yield percent of 95% by lyophilizing the filtrate.

HPLC analysis condition: (UG-120 (250×4.6 mm), developing solvent: 25 mM ammonia acetate aqueous solution:acetonitrile=78:22, 0.70 ml/min)

$^1$H-NMR (400 MHz, $D_2O$, external standard: acetone ($^1$H: 2.61 ppm)

δ 5.03 (s, 1H, Man4-H-1), 4.99 (d, 1H, GlcNAc1-H-1), 4.53 (d, 1H, GlcNAc2-H-1), 4.47 (d, 2H, GlcNAc5,5'-H-1), 4.16 (bs, 1H, Man3-H-2), 4.10 (bd, 1H, Man4-H-2), 4.02 (bd, 1H, Man4'-H-2), 2.83 (dd, 1H, Asn($CH_2$)), 2.75 (dd, 1H, Asn($CH_2$)), 1.99, 1.97, 1.93 (s, 12H, Ac×4)

MALDI-MS: Calcd for $C_{54}H_{90}N_6O_{38}$ [M+Na]$^+$ 1453.519, found 1453.384.

(Example 8) Synthesis of DiGlcNAc Sugar Chain-NH—AcBr

The DiGlcNAc sugar chain asparagine synthesized in Example 7 (0.7 g, 0.5 mmol) was dissolved in 0.5 M NaHCO$_3$ aqueous solution (17.4 mL), and cooled for 1 hour at 4° C. After 1 hour, immobilized GA enzyme (about 5 mL) was added, and stirred at 4° C. One hour after the start of reaction, after confirming the completion of the reaction by the disappearance of the source material peak eluting at 12 minutes and the confirmation of a new peak eluting at 21 minutes in HPLC analysis, the immobilized enzyme was removed by filtration. After adding NaHCO$_3$ (2.0 g, 33.4 mmol) to the filtrate obtained, bromoacetyl bromide (1.1 mL, 16.7 mmol) dissolved in DCM (16.7 mL) was added, and stirred under ice-cooling. The completion of the reaction was confirmed by the disappearance of the source material peak eluting at 21 minutes and the confirmation of a new peak eluting at 29 minutes in HPLC analysis. This reaction with bromoacetyl bromide was completed in an hour or less. After confirmation of the completion of the reaction, the DCM phase was removed by partitioning, and the aqueous phase was purified with gel filtration column chromatography (Sephadex G25, 2.3 cm×100 cm, water, flow rate 1.0 ml/min). The fraction comprising the sugar chain was concentrated and lyophilized to obtain DiGlcNAc sugar chain bromoacetamide at a yield amount of 0.6 g and a yield percent of 88%. As a result of analyzing the sugar chain compound obtained, the α isomer abundance ratio thereof was 1.0% or less (in all cases when experimented with n=2).

HPLC analysis condition: (Hydrosphere 250×4.6 mm, developing solvent A: 25 mM ammonia acetate aqueous solution, B: acetonitrile, gradient: A 100% 0.70 ml/min→A 90% 0.70 ml/min, 30 minutes)

$^1$H-NMR (400 MHz, $D_2O$, external standard: acetone ($^1$H: 2.61 ppm)

δ 5.03 (s, 1H, Man4-H-1), 4.99 (d, 1H, GlcNAc1-H-1), 4.83 (s, 1H, Man4'-H-1), 4.53 (d, 1H, GlcNAc2-H-1), 4.47 (d, 2H, GlcNAc5,5'-H-1), 4.17 (bs, 1H, Man3-H-2), 4.10 (bd, 1H, Man4-H-2), 4.02 (bd, 1H, Man4'-H-2), 1.99, 1.97, 1.92 (s, 18H, Ac×6)

MALDI-MS: Calcd for $C_{52}H_{86}BrN_5O_{36}$ [M+Na]$^+$ 1458.413, found 1458.575.

(Example 9) Synthesis of Disialo Sugar Chain Asparagine-Fmoc Wherein Carboxylic Add of Sialic Add is Amidated The disialo sugar chain asparagine-Fmoc wherein the carboxylic add of the sialic add is protected with a phenacyl ester group synthesized in Reference Example 4 (3.0 g, 1.1 mmol) was dissolved in saturated ammonium hydrogen carbonate aqueous solution (30 mL), and stirred for 3 hours. The precipitate produced during the reaction was removed by centrifugation, the supernatant was desalted with gel filtration column chromatography (Sephadex G25, 2.3 cm×100 cm, water, flow rate 1.0 ml/min), and the fraction comprising the sugar chain was collected, concentrated, and lyophilized. The sugar chain compound after lyophilization was dissolved in water (60 mL), NaHCO$_3$ (900 mg) and Fmoc-OSu (1.8 g) dissolved in DMF (30 mL) were added under ice-cooling, and stirred at room temperature. Twelve hours after the start of reaction, the reaction solution was added to acetone (500 mL) to precipitate the sugar chain. The precipitate was collected by centrifugation, and dried at ordinary temperature and pressure. After drying, the residue obtained was dissolved in water, and purified by HPLC to obtain disialo sugar chain asparagine-Fmoc wherein the carboxylic add of the sialic add is amidated ("—COOH" became "—CONH$_2$") at a yield amount of 1.1 g and a yield percent of 40.0%.

(Hipersep LC200 Kromasil 13C18 200×250 mm, developing solvent 25 mM NH$_4$OAc aqueous solution:acetonitrile=85:15, 1.883 L/min)

MALDI-MS: Calcd for $C_{103}H_{156}N_{10}O_{64}$ [M+Na]$^+$ 2579.916, found 2580.103.

The chemical structure of the sialic add moiety when the carboxylic add of the sialic acid is protected with a phenacyl ester group employed in Example 9 can be represented by the formula below (the following formula shows only the protected sialic add portion.)

[Chemical Formula 28]

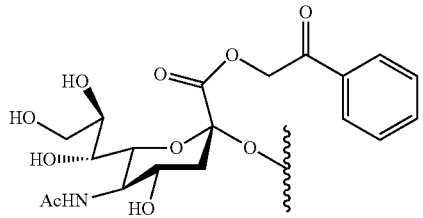

(Example 10) Synthesis of Disialo Sugar Chain-NH—AcBr Wherein Carboxylic Add of Sialic Add is Amidated The disialo sugar chain asparagine-Fmoc wherein the carboxylic add of the sialic add is amidated obtained in Example 9 (1.0 g, 0.4 mmol) was dissolved in 25% ammonia water (15 mL), and stirred at 37° C. After 4 hours, the completion of the reaction was confirmed by the disappearance of the source material peak eluting at 11 minutes in HPLC analysis. The insoluble matter produced during the reaction was removed by filtration, and the filtrate was lyophilized. After lyophilization, this was dissolved in 0.5 M NaHCO$_3$ aqueous solution, and cooled for 1 hour at 4° C. After 1 hour, immobilized GA enzyme (about 5.0 mL) was added, and stirred at 4° C. One hour after the start of reaction, the completion of the reaction was confirmed with HPLC, and the immobilized enzyme was removed by filtration. After adding NaHCO$_3$ (3.6 g, 41.6 mmol) to the filtrate obtained, bromoacetyl bromide (1.8 mL, 20.8 mmol) dissolved in DCM (6.5 mL) was added, and stirred under ice-cooling. This reaction with bromoacetyl bromide was completed in an hour or less. After confirmation of the completion of the reaction, the DCM phase was removed by partitioning, the aqueous phase was purified with gel filtration column chromatography (Sephadex G25, 2.3 cm×100 cm, water, flow rate 1.0 ml/min), and concentrated and lyophilized to obtain disialo sugar chain bromoacetamide wherein the carboxylic add of the sialic add is amidated (disialo sugar chain-NH—AcBr wherein the carboxylic add of the sialic acid is amidated) at a yield amount of 0.5 g and a yield percent of 52%. As a result of analyzing the sugar chain obtained, the α isomer abundance ratio thereof was 0.8%.

$^1$H-NMR (400 MHz, $D_2O$, external standard: acetone ($^1$H: 2.61 ppm)

δ 5.07 (s, 1H, Man4-H-1), 5.01 (d, 1H, GlcNAc1-H-1), 4.88 (s, 1H, Man4'-H-1), 4.55 (m, 3H, GlcNAc2,5,5'-H-1), 4.39 (d, 2H, Gal6,6'-H-1), 4.20 (bs, 1H, Man3-H-2), 4.14 (bd, 1H, Man4-H-2), 4.06 (bd, 1H, Man4'-H-2), 2.62 ((bdd, 2H, NeuAc7,7'-H-3 eq), 2.04, 2.04, 2.00, 1.98, 1.95 (m, 18H, Ac×6), 1.78 (dd, 2H, NeuAc7,7'-H-3 ax)

MALDI-MS: Calcd for $C_{86}H_{142}BrN_9O_{60}$ [M+Na]$^+$ 2362.742, found 2362.484.

Various derivatives were synthesized next with the benzyl esterified disialo sugar chain bromoacetamide synthesized in Example 2 (diBn disialo sugar chain-NH—AcBr) and the disialo sugar chain-NH—AcBr synthesized in Example 4 as source materials.

(Example 11) Synthesis of diBn Disialo Sugar Chain-NH—AcCl

The diBn disialo sugar chain-NH—AcBr synthesized in Example 2 (30.8 mg, 122 μmol) was dissolved in water (950 μL), sodium chloride (NaCl, 60.0 mg, 1.0 mmol) was added, and stirred at room temperature. After 96 hours, the completion of the reaction was confirmed by the disappearance of the source material peak eluting at 28 minutes and the confirmation of a new peak eluting at 26 minutes in HPLC analysis. Upon confirmation of the completion of the reaction, the reaction solution was purified with gel filtration column chromatography (Sephadex G25, 1.5 cm×45 cm, water, flow rate 0.7 ml/min). The fraction comprising the sugar chain was concentrated and lyophilized to obtain diBn-disialo-AcCl at a yield amount of 22.3 mg and a yield percent of 74%.

$^1$H-NMR (400 MHz, $D_2O$, external standard: acetone ($^1$H: 2.61 ppm)

δ 7.40 (m, 10H, Ar), 5.28 (d, 1H, Bn-C$\underline{H}_2$), 5.21 (d, 1H, Bn-C$\underline{H}_{12}$), 5.02 (s, 1H, Man4-H-1), 4.99 (d, 1H, GlcNAc1-H-1), 4.84 (s, 1H, Man4'-H-1), 4.67 (s, 1H, Man3-H-1), 4.51 (m, 3H, GlcNAc2,5,5'-H-1), 423 (d, 2H, Gal6,6'-H-1), 4.15 (bs, 1H, Man3-H-2), 4.10 (bd, 1H, Man4-H-2), 4.02 (bd, 1H, Man4'-H-2), 2.59 (m, 2H, NeuAc7,7'-H-3 eq), 1.98, 1.94, 1.92, 1.91 (m, 18H, Ac×6), 1.75 (dd, 2H, NeuAc7,7'-H-3 ax)

MALDI-MS: Calcd for $C_{100}H_{152}ClN_7O_{62}$ [M+Na]$^+$ 2502.729, found 2501.034.

(Example 12) Synthesis of diBn Disialo Sugar Chain-NH—AcI

The diBn disialo sugar chain-NH—AcBr synthesized in Example 2 (30.9 mg, 122 μmol) was dissolved in water (900 μL), sodium iodide (NaI, 150.0 mg, 1.0 mmol) was added, and stirred at room temperature. After 2 hours, the completion of the reaction was confirmed by the disappearance of the source material peak eluting at 28 minutes and the confirmation of a new peak eluting at 31 minutes in HPLC analysis. After confirmation of the completion of the reaction, the reaction solution was purified with gel filtration column chromatography (Sephadex G25, 1.5 cm×45 cm, water, flow rate 0.7 ml/min). The fraction comprising the sugar chain was concentrated and lyophilized to obtain diBn-disialo sugar chain-NH-AdI at a yield amount of 28.5 mg and a yield percent of 91%.

$^1$H-NMR (400 MHz, $D_2O$, external standard: acetone ($^1$H: 2.61 ppm)

δ 7.41 (m, 10H, Ar), 5.29 (d, 1H, Bn-C$\underline{H}_2$), 5.22 (d, 1H, Bn-C$\underline{H}_2$), 5.04 (s, 1H, Man4-H-1), 4.96 (d, 1H, GlcNAc1-H-1), 4.85 (s, 1H, Man4'-H-1), 4.68 (s, 1H, Man3-H-1), 4.51 (m, 3H, GlcNAc2,5,5'-H-1), 424 (d, 2H, Gal6,6'-H-1), 4.16 (bs, 1H, Man3-H-2), 4.10 (bd, 1H, Man4-H-2), 4.02 (bd, 1H, Man4'-H-2), 2.59 (m, 2H, NeuAc7,7'-H-3 eq), 1.99, 1.95, 1.93, (m, 18H, Ac×6), 1.75 (dd, 2H, NeuAc7,7'-H-3 ax)

MALDI-MS: Calcd for $C_{100}H_{152}ClN_7O_{62}$ [M+Na]$^+$ 2592.790, found 2592.929.

(Example 13) DiBn Disialo Sugar Chain-NH—AcN$_3$

The diBn disialo sugar chain-NH—AcBr synthesized in Example 2 (51.9 mg, 20.6 μmol) was dissolved in DMF (1 mL), sodium azide (NaN$_3$, 64.4 mg, 990.4 μmol) was added, and stirred at 37° C. After 6 hours, the completion of the reaction was confirmed by the disappearance of the source material peak eluting at 26 minutes and the confirmation of a new peak eluting at 28 minutes in HPLC analysis. After confirmation of the completion of the reaction, the reaction solution was added into ethyl acetate (EtOAc, 4 mL) to precipitate the sugar chain component. The precipitate was collected by centrifugation by a centrifugal separator, and the residue collected was aliquoted with HPLC to obtain diBn disialo sugar chain-NH—AcN$_3$ at a yield amount of 35.3 mg and a yield percent of 69%.

HPLC analysis condition: (UG-120 250×4.6 mm, developing solvent: water:acetonitrile=86:14, 0.70 ml/min)

HPLC preparative condition: (UG-120 250×20 mm, developing solvent water:acetonitrile=86:14, 7.0 ml/min)

$^1$H-NMR (400 MHz, $D_2O$, external standard: acetone ($^1$H: 2.61 ppm)

δ 7.40 (m, 10H, Ar), 5.28 (d, 1H, Bn-C$\underline{H}_2$), 5.21 (d, 1H, Bn-C$\underline{H}_2$), 5.03 (s, 1H, Man4-H-1), 4.99 (d, 1H, GlcNAc1-H-1), 4.84 (s, 1H, Man4'-H-1), 4.67 (s, 1H, Man3-H-1), 4.51 (m, 3H, GlcNAc2,5,5'-H-1), 423 (d, 2H, Gal6,6'-H-1), 4.15 (bs, 1H, Man3-H-2), 4.10 (bd, 1H, Man4-H-2), 4.02 (bd, 1H, Man4'-H-2), 2.58 (m, 2H, NeuAc7,7'-H-3 eq), 1.98, 1.94, 1.92, 1.91 (m, 18H, Ac×6), 1.79 (dd, 2H, NeuAc7,7'-H-3 ax)

MALDI-MS: Calcd for $C_{100}H_{152}N_{10}O_{62}$ [M+Na]$^+$ 2507.895, found 2507.702.

(Example 14) Disialo Sugar Chain-NH—AcNHNH$_2$

The disialo sugar chain-AcBr synthesized in Example 4 (90.9 mg, 38.8 μmol) was dissolved in 0.1 M phosphate buffer (pH=7.4), hydrazine monohydrate (10 μL) was added, and stirred at room temperature. After 7 hours, the completion of the reaction was confirmed by the disappearance of the source material peak eluting at 12 minutes and the confirmation of a new peak eluting at 10 minutes in HPLC analysis. After confirmation of the completion of the reaction, acetic add (20 μL) was added for neutralization, and this was purified with gel filtration column chromatography (Sephadex G25, 1.5 cm×45 cm, water, flow rate 0.7 ml/min). The fraction comprising the sugar chain was concentrated and lyophilized to obtain disialo sugar chain-NH—AcNHNH$_2$ at a yield amount of 82.5 mg and a yield percent of 93%.

HPLC analysis condition: (Hydrosphere 250×4.6 mm, developing solvent A: 25 mM ammonia acetate aqueous solution, B: acetonitrile, gradient: A 98% 0.70 ml/min→A 65% 0.70 ml/min, 30 minutes)

$^1$H-NMR (400 MHz, D$_2$O, external standard: acetone ($^1$H: 2.61 ppm)

δ 5.06 (s, 1H, Man4-H-1), 5.03 (d, 1H, GlcNAc1-H-1), 4.88 (s, 1H, Man4'-H-1), 4.54 (m, 3H, GlcNAc2,5,5'-H-1), 4.38 (d, 2H, Gal6,6'-H-1), 4.18 (bs, 1H, Man3-H-2), 4.12 (bd, 1H, Man4'-H-2), 4.05 (bd, 1H, Man4'-H-2), 2.60 (m, 2H, NeuAc7,7'-H-3 eq), 2.01, 2.00, 1.96, 1.93 (m, 18H, Ac×6), 1.66 (dd, 2H, NeuAc7,7'-H-3 ax)

ESI-MS: Calcd for C$_{86}$H$_{143}$N$_9$O$_{62}$ [M+2H]$^{2+}$ 1147.916, [M+3H]$^3$+765.610, found 1147.930, 765.620.

(Example 15) DiBn Disialo Sugar Chain-NH—Ac—SH

The diBn disialo sugar chain-NH—AcBr synthesized in Example 2 (972 mg, 38.5 μmol) was dissolved in 0.1 M phosphate buffer (pH=7.4, 2 mL), thioacetic acid (5 μL, 61.4 μmol) was added, and stirred at room temperature. After 1 hour, the completion of the reaction was confirmed by the disappearance of the source material peak eluting at 23 minutes and the confirmation of a new peak eluting at 24 minutes in HPLC analysis. Subsequently, 2-mercaptoethanesulfonate sodium (MESNA, 162.0 mg, 986.7 μmol) was added to the reaction solution, and stirred at room temperature. After 44 hours, the completion of the reaction was confirmed by the attenuation of the source material peak eluting at 24 minutes and the confirmation of a new peak eluting at 22 minutes in HPLC analysis. After confirmation of the completion of the reaction, this was aliquoted with HPLC, the fraction comprising the sugar chain of interest was desalted by gel filtration column chromatography (Sephadex G25, 1.5 cm×45 cm, water, flow rate 0.4 ml/min), and the fraction comprising the sugar chain was concentrated and lyophilized to obtain diBn disialo sugar chain-NH—Ac—SH at a yield amount of 48 mg and a yield percent of 50%.

HPLC analysis condition: (UG-120 250×4.6 mm, developing solvent A: 25 mM ammonia acetate aqueous solution, B: acetonitrile, gradient: A 90% 0.70 ml/min→A 70% 0.70 ml/min, 30 minutes)

HPLC preparative condition: (UG-120 250×4.6 mm, developing solvent A: 25 mM ammonia acetate aqueous solution, B: acetonitrile, gradient: A 90% 0.70 ml/min→A 70% 7.00 ml/min, 30 minutes)

$^1$H-NMR (400 MHz, D$_2$O, external standard: acetone ($^1$H: 2.61 ppm)

δ 7.40 (m, 10H, Ar), 5.29 (d, 1H, Bn-C$\underline{H}_2$), 5.22 (d, 1H, Bn-C$\underline{H}_2$), 5.03 (s, 1H, Man4-H-1), 4.96 (d, 1H, GlcNAc1-H-1), 4.84 (s, 1H, Man4'-H-1), 4.51 (m, 3H, GlcNAc2,5,5'-H-1), 424 (d, 2H, Gal6,6'-H-1), 4.15 (bs, 1H, Man3-H-2), 4.09 (bd, 1H, Man4-H-2), 4.01 (bd, 1H, Man4'-H-2), 3.13 (dd, 2H, —COC$\underline{H}_2$SH), 2.58 (m, 2H, NeuAc7,7'-H-3 eq), 1.98, 1.94, 1.92, 1.91 (m, 18H, Ac×6), 1.75 (dd, 2H, NeuAc7,7'-H-3 ax)

MALDI-MS: Calcd for C$_{100}$H$_{153}$N$_7$O$_{62}$S [M+Na]$^+$ 2498.865, found 2499.051.

(Example 16) DiBn Disialo Sugar Chain-NH—Ac—SCH$_2$CH$_2$NH$_2$

The diBn disialo sugar chain-NH—AcBr synthesized in Example 2 (106.4 mg, 42.2 μmol) was dissolved in 61 mM cysteamine and 0.1 M phosphate buffer (pH=7.0, 4 mL) comprising 20 mM tris-2-carboxyethyl phosphine hydrochloride salt (TCEP), and stirred at room temperature. After 20 hours, the completion of the reaction was confirmed by the disappearance of the source material peak eluting at 23 minutes and the confirmation of a new peak eluting at 19 minutes in HPLC analysis. After confirmation of the completion of the reaction, this was aliquoted with HPLC, the fraction comprising the sugar chain of interest was desalted by gel filtration column chromatography (Sephadex G25, 1.5 cm×45 cm, water, flow rate 0.4 ml/min), and the fraction comprising the sugar chain was concentrated and lyophilized to obtain diBn disialo sugar chain-NH—Ac—SCH$_2$CH$_2$NH$_2$ at a yield amount of 63 mg and a yield percent of 59%.

HPLC analysis condition: (UG-120 250×4.6 mm, developing solvent A: 25 mM ammonia acetate aqueous solution, B: acetonitrile, gradient: A 90% 0.70 ml/min→A 70% 0.70 ml/min, 30 minutes)

HPLC preparative condition: (UG-120 250×4.6 mm, developing solvent: 25 mM ammonia acetate aqueous solution:acetonitrile=85:15, 7.00 ml/min, 30 minutes)

$^1$H-NMR (400 MHz, D$_2$O, external standard: acetone ($^1$H: 2.61 ppm)

δ 7.40 (m, 10H, Ar), 5.29 (d, 1H, Bn-C$\underline{H}_2$), 5.22 (d, 1H, Bn-C$\underline{H}_2$), 5.03 (s, 1H, Man4-H-1), 4.98 (d, 1H, GlcNAc1-H-1), 4.84 (s, 1H, Man4'-H-1), 4.50 (m, 3H, GlcNAc2,5,5'-H-1), 424 (d, 2H, Gal6,6'-H-1), 4.15 (bs, 1H, Man3-H-2), 4.09 (bd, 1H, Man4-H-2), 4.01 (bd, 1H, Man4'-H-2), 3.23 (bs, 2H, —COC$\underline{H}_2$S—), 3.12 (m, 2H, —SC$\underline{H}_2$CH$_2$NH$_2$—), 2.78 (m, 2H, —SCH$_2$C$\underline{H}_2$NH$_2$—), 2.58 (m, 2H, NeuAc7, 7'-H-3 eq), 1.98, 1.94, 1.92, 1.91 (m, 18H, Ac×6), 1.75 (dd, 2H, NeuAc7,7'-H-3 ax)

MALDI-MS: Calcd for C$_{102}$H$_{158}$N$_8$O$_{62}$S [M+Na]$^+$ 2541.907, found 2542.020.

(Example 17) DiBn Disialo Sugar Chain-NH—Ac—CH(OMe)$_2$

The benzyl esterified disialo sugar chain asparagine-Fmoc of Reference Example 3 (109.6 m g, 40.0 μmol) was dissolved in dimethylformamide (DMF, 1.1 mL), piperidine (16 μL, 160.1 μmol) was added, and allowed to react at room temperature. After 30 minutes, the completion of the reaction was confirmed by the disappearance of the source material peak eluting at 20 minutes and the confirmation of a new peak eluting at β minutes in HPLC analysis (analysis condition (1)). After confirmation of the completion of the reaction, the reaction solution was added to ethyl acetate (10.0 mL) to precipitate the sugar chain. The sugar chain component precipitated by centrifugation was collected. After drying the residue obtained at ordinary temperature and pressure, this was dissolved in 1 M sodium acetate aqueous solution (pH=5.0, 3 mL), purified by gel filtration column chromatography (Sephadex G25, 1.5 cm×45 cm, water, flow rate 0.4 ml/min), and the fraction comprising the sugar chain was concentrated and lyophilized to obtain diBn disialo sugar chain-Asn at a yield amount of 100.8 mg and a yield percent of 100%. The diBn disialo sugar chain-Asn obtained was dissolved in 0.5 M NaHCO$_3$ aqueous solution (1 mL), and cooled for 1 hour under ice-cooling. After 1 hour, immobilized GA enzyme (about 500 μL) was added, and stirred under ice-cooling. One and a half hours after the start of reaction, upon confirming the completion of the reaction by the disappearance of the source material peak eluting at 11 minutes and the confirmation of a new peak eluting at β minutes in HPLC analysis (analysis condition (2)), the immobilized enzyme was removed by filtration. After adding NaHCO$_3$ (38.0 mg, 452.4 μmol) to the filtrate obtained, 3,3 dimethoxypropionic add-hydroxysuccinimide ester (200.5 mg, 8672 μmol) dissolved in DMF (1.5 mL) was added, and stirred under ice-cooling. After 30 minutes, the temperature was raised to room temperature and stirring was continued. After 20 hours, the completion of the reaction was confirmed by the disappearance of the source material peak eluting at β minutes and the confirmation of a new peak eluting at 20 minutes in HPLC analysis (analysis condition (2)). After confirmation of the completion of the reaction, this was purified with gel filtration column chromatography (Sephadex G25, 1.5 cm×45 cm, water, flow rate 0.4 ml/min). The fraction comprising the sugar chain was concentrated and lyophilized to obtain diBn disialo sugar chain-NH—Ac—CH(OMe)$_2$ at a yield amount of 79 mg and a yield percent of 79%. As a result of analyzing the sugar chain obtained, the α isomer abundance ratio thereof was 0.1% or less.

HPLC analysis condition (1): (UG-120 250×4.6 mm, developing solvent A: 25 mM ammonia acetate aqueous solution, B: acetonitrile, gradient: A 90% 0.70 ml/min→A 40% 0.70 ml/min, 30 minutes)

HPLC analysis condition (2): (UG-120 250×4.6 mm, developing solvent A: 25 mM ammonia acetate aqueous solution, B: acetonitrile, gradient: A 90% 0.70 ml/min→A 70% 0.70 ml/min, 30 minutes)

$^1$H-NMR (400 MHz, D$_2$O, external standard: acetone ($^1$H: 2.61 ppm)

δ 7.40 (m, 10H, Ar), 5.28 (d, 1H, Bn-C$\underline{H}_2$), 5.22 (d, 1H, Bn-C$\underline{H}_2$), 5.03 (s, 1H, Man4-H-1), 4.97 (d, 1H, GlcNAc1-H-1), 4.84 (s, 1H, Man4'-H-1), 4.50 (m, 3H, GlcNAc2,5,5'-H-1), 4.23 (d, 2H, Gal6,6'-H-1), 4.15 (bs, 1H, Man3-H-2), 4.09 (bd, 1H, Man4-H-2), 4.01 (bd, 1H, Man4'-H-2), 2.58 (m, 2H, NeuAc7,7'-H-3 eq), 2.55 (m, 2H, C$\underline{H}_2$ (OMe)$_2$), 1.98, 1.94, 1.92 (m, 18H, Ac×6), 1.75 (dd, 2H, NeuAc7,7'-H-3 ax)

MALDI-MS: Calcd for C$_{103}$H$_{159}$N$_7$O$_{64}$ [M+Na]$^+$ 2540.930, found 2541.123.

COMPARATIVE EXAMPLES (Comparative Example 1) Preparation of Activated Sugar Chain by Conventional Method Sialylglycopeptide (SGP) (100 mg) was dissolved in 50 mM phosphate buffer at pH 7.0, and PNGase F (BioLabs Inc., 1 U) was added. This was incubated at 37° C. for 24 hours, and lyophilized upon confirmation of the completion of the reaction with TLC. The lyophilizate was purified with gel filtration column chromatography (Sephadex G25, 1.5 cm×30 cm, water, flow rate 1.0 ml/min) to obtain disialo sugar chain-OH at a yield amount of 74 mg.

The disialo sugar chain-OH obtained (10 mg) was dissolved in saturated ammonium hydrogen carbonate aqueous solution and prepared to 30 mM. This was reacted at room temperature, and a saturated state was maintained at all times. After reacting for 7 days and the reaction was considered almost complete with TLC, the reaction solution was directly lyophilized. Lyophilization was repeated three times in order to remove ammonium hydrogen carbonate, and 9 mg of powder comprising an aminated disialo sugar chain was obtained.

The powder obtained comprising an aminated disialo sugar chain (5 mg) was dissolved in water (100 μL), and sodium hydrogen carbonate (2 mg) was added. To this was added bromoacetyl bromide (8.0 μL, 92.5 μmol) dissolved in dichloromethane (DCM, 100 μL), and stirred under ice-cooling. After 1.5 hours, the completion of the reaction was confirmed with TLC, this was neutralized with sodium hydrogen carbonate, filtered, and then concentrated under reduced pressure. Subsequently, this was purified with gel filtration column chromatography (Sephadex G25, 1.5 cm×30 cm, water, flow rate 1.0 ml/min). The fraction comprising the sugar chain was concentrated and lyophilized to obtain disialo sugar chain bromoacetamide at a yield amount of 4 mg and a yield percent of 77%. As a result of analyzing the sugar chain obtained, the α isomer abundance ratio thereof was 9.1%. Although it was speculated that there was also residual source material in this reaction, calculation of the residual amount of the source material was difficult.

(Comparative Example 2) Preparation of Activated Sugar Chain by Conventional Method Asialo sugar chain-OH (from Glytech. Inc., 500.0 mg, 304.6 μmol) was dissolved in water (5 mL), ammonium hydrogen carbonate was added so that the aqueous solution is saturated, and stirred at 30° C. After reacting for 6 days and the reaction was confirmed to be almost complete with TLC, excess ammonium hydrogen carbonate was removed from the reaction solution by concentration, azeotropy, and lyophilization. After lyophilization, the powder obtained comprising an aminated asialo sugar chain (250 mg, 152.1 μmol) was dissolved in water (2 mL), NaHCO$_3$ (269.6 mg, 3.2 mmol) was added, and stirred under ice-cooling. After 20 minutes, bromoacetyl bromide (140.2 μL, 1.6 mmol) dissolved in DCM (1.5 mL) was added, and stirred under ice-cooling. After 2 hours, the completion of the reaction was confirmed by the disappearance of the source material peak eluting around 14 minutes and the confirmation of a new peak eluting around 21 minutes in HPLC analysis. After confirmation of the completion of the reaction, the DCM phase was removed by partitioning, and only the aqueous layer was purified with gel filtration column chromatography (Sephadex G25, 1.5 cm×30 cm, water, flow rate 0.4 ml/min). The fraction comprising the sugar chain was concentrated and lyophilized to obtain a mixture comprising asialo sugar chain bromoacetamide at a yield amount of 235.0 mg and a yield percent of 88%. As a result of analyzing the mixture obtained with $^1$H-NMR, 68.5% of the asialo sugar chain bromoacetamide which is the sugar chain of interest, α isomer at an abundance ratio of 6.5%, and about 25% of the source material were mixed. This $^1$H-NMR spectrum is shown in FIG. 3. As shown in FIG. 3, when the conventional method was employed, signals derived from a anomer and the source material in addition to the main product β anomer were confirmed.

Accordingly, residual source material was confirmed when synthesized with the conventional method, but as already described in Example 6, the source material being mixed was not confirmed in the synthesis method of the present invention (see FIG. 4).

It was shown by this comparison that the method of the present invention is a manufacturing method which is superior to the conventional method not only in β selectivity but also in yield in a short period of time.

(Comparative Example 3) Preparation of diBn Disialo Sugar Chain-NH$_2$ by Conventional Method DiBn disialo sugar chain-OH (from Glytech. Inc., 98.7 mg, 41.1 μmol) was dissolved in water (1.0 mL), ammonium hydrogen carbonate was added so that the aqueous solution is saturated, and stirred at 30° C. Upon tracking the reaction with TLC, it was confirmed that multiple products were produced after 22 hours. Excess ammonium hydrogen carbonate was thus removed by concentration, azeotropy, and lyophilization. After lyophilization, the deprotection of the benzyl ester could be confirmed by NMR and ESI-MS. It was suggested by the integrated intensity ratio of NMR that approximately 30% of the benzyl ester groups were deprotected. From the above result, it is thought that efficient synthesis of diBn disialo-NH$_2$ with the conventional method is difficult. Accordingly, it is also thought that synthesis of benzyl esterified disialo sugar chain bromoacetamide employing the above as the intermediate is also difficult.

ESI-MS:

diBn disialo-OH; Calcd for $C_{98}H_{150}N_6O_{62}$ [M+2H]$^+$ 1202.44, found 1201.96.

monoBn disialo-OH; Calcd for $C_{91}H_{144}N_6O_{62}$ [M+2H]$^+$ 1157.42, found 1156.95.

SEQUENCE LISTING

Sequence listing.TXT to obtain a compound represented by the following Formula (3):

$$G\text{-}NH_2 \quad (3)$$

(wherein G represents a sugar chain, NH$_2$ represents an amino group, and G and NH$_2$ are bound so that the nitrogen atom derived from the nitrogen atom of the side chain of said asparagine is bound to the reducing terminal of said sugar chain in β configuration), (wherein step (a) is performed at 0° C. to 10° C.; and (b) a step of reacting the compound represented by said Formula (3) obtained in step (a) with a compound represented by the following Formula (4)

$$L^1\text{-}CO\text{-}CH_2\text{-}Y^1 \quad (4)$$

(wherein L$^1$ is a leaving group, and Y$^1$ is an activating group).

2. A method for manufacturing a compound according to claim 1, wherein step (b) is a step of reacting the compound represented by said Formula (3) obtained in step (a) with a compound represented by the following Formula (5)

$$L^1\text{-}CO\text{-}CH_2\text{-}Z \quad (5)$$

(wherein L1 is a leaving group, and Z is a halogen atom); and

---

---

The invention claimed is:

1. A method for manufacturing a compound represented by the following Formula (1a):

$$G\text{-}NH\text{-}CO\text{-}CH_2\text{-}Y^1 \quad (1a)$$

(wherein G represents a sugar chain, Y$^1$ represents an activating group, and G and NH are bound so that the nitrogen atom of NH is bound to the reducing terminal of said sugar chain in β configuration) comprising the following steps (a)-(b):

(a) a step of applying a sugar chain asparagine hydrolase under basic conditions on a compound having the sugar chain asparagine structure represented by the following Formula (2):

$$G\text{-}Asn \quad (2)$$

(wherein G represents a sugar chain, Asn represents an asparagine, and G and Asn are bound so that the nitrogen atom of the side chain of said asparagine is bound to the reducing terminal of said sugar chain in β configuration)

which further comprises a step (c) of reacting the compound obtained in step (b) with a compound represented by the following Formula (6a) or Formula (6b):

$$L^2\text{-}Y^2 \quad (6a)$$

(wherein L$^2$ is a leaving group, and Y$^2$ is an activating group)

$$L^3Y^3 \quad (6b)$$

(wherein L$^3$ is a cation, Y$^3$ is an anion of said activating group Y$^2$, and L$^3$Y$^3$ is a salt of L$^3$ and Y$^3$).

3. A method for manufacturing a compound according to claim 1, characterized in that Y$^1$ is selected from the group consisting of a bromine atom, a chlorine atom, an iodine atom, SH, N$_3$, NHNH$_2$, SHCH$_2$CH$_2$NH$_2$, and CH(OMe)$_2$.

4. A method for manufacturing a compound according to claim 2, characterized in that:

Z is a bromine atom, and

Y$^2$ is selected from the group consisting of a chlorine atom, an iodine atom, SH, N$_3$, NHNH$_2$, and SHCH$_2$CH$_2$NH$_2$.

5. A method for manufacturing a compound according to claim 1, characterized in that said sugar chain asparagine hydrolase in said step (a) is glycosylasparaginase (GA) and/or peptide:N-glycanase (PNGase).

6. A method for manufacturing a compound according to claim 1, characterized in that said sugar chain asparagine hydrolase in said step (a) is immobilized to a carrier.

7. A method for manufacturing a compound according to claim 1, characterized in that said sugar chain asparagine hydrolase in said step (a) is immobilized to a carrier,
and further comprising the following step (d) after said step (a) and before said step (b):
(d) a step of separating said sugar chain asparagine hydrolase immobilized to a carrier from the reaction system.

8. A method for manufacturing a compound according to claim 1, characterized in that said sugar chain is an N-linked sugar chain.

9. A method for manufacturing a compound according to claim 1, characterized in that said sugar chain is an N-linked complex-type sugar chain.

10. A method for manufacturing a compound according to claim 1, characterized in that said sugar chain is a sugar chain selected from the group consisting of a disialo sugar chain, an asialo sugar chain, and a DiGlcNAc sugar chain.

11. A method for manufacturing a compound according to claim 1, characterized in that said sugar chain is those represented by the following Formula (7):

[Chemical Formula 1]

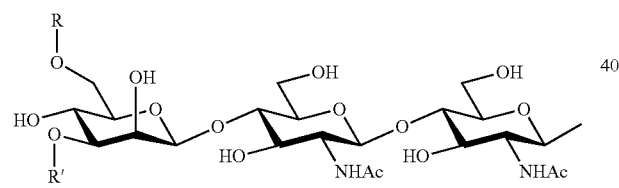

(7)

wherein R and R' are each independently selected from the group consisting of sugar chains represented by the following Formula (8a) to Formula (8f):

[Chemical Formula 2]

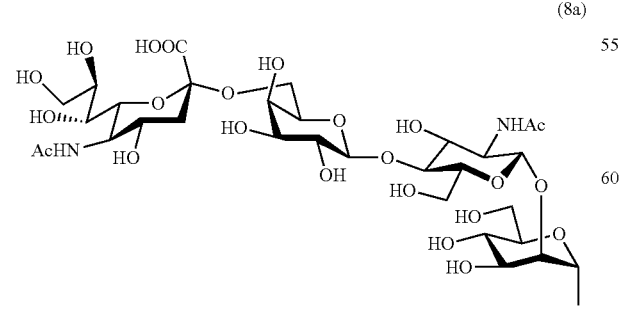

(8a)

[Chemical Formula 3]

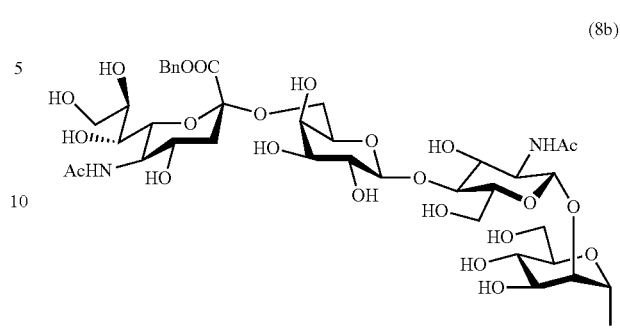

(8b)

[Chemical Formula 4]

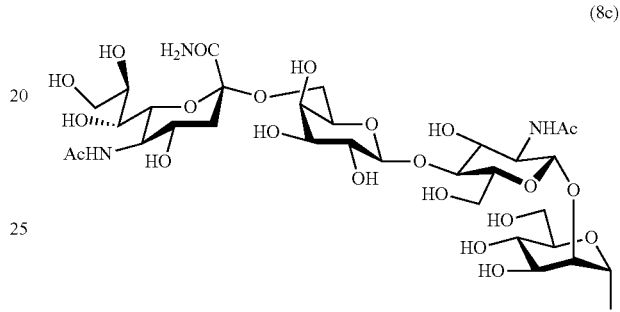

(8c)

[Chemical Formula 5]

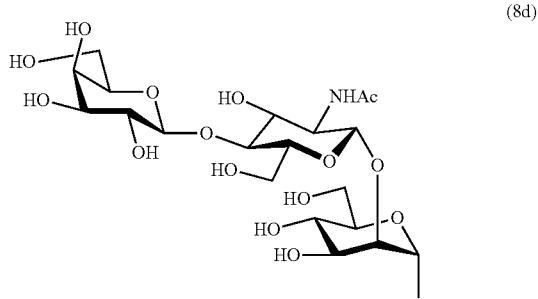

(8d)

[Chemical Formula 6]

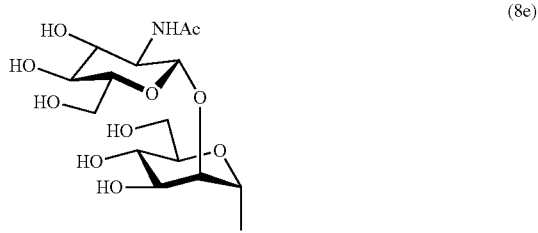

(8e)

[Chemical Formula 7]

(8f)

12. A method for manufacturing a compound according to claim 1, characterized in that said sugar chain is a disialo sugar chain wherein the side chain carboxylic acid of the sialic acid configuring said disialo sugar chain is protected by esterification or amidation.

* * * * *